(12) United States Patent
Chung et al.

(10) Patent No.: US 10,473,615 B2
(45) Date of Patent: Nov. 12, 2019

(54) POROUS PROTECTIVE LAYER FOR GAS SENSOR, METHOD FOR PRODUCING SAME, AND GAS SENSOR COMPRISING SAME

(71) Applicant: AMOTECH CO., LTD., Incheon (KR)

(72) Inventors: Yeon-Soo Chung, Incheon (KR); Kil Jin Park, Incheon (KR); Sung-Jin Hong, Gyeonggi-do (KR); Soo-Min Oh, Seoul (KR); Eun-Ji Kim, Incheon (KR)

(73) Assignee: AMOTECH CO., LTD., Incheon (KR)

( * ) Notice: Subject to any disclaimer, the term of this patent is extended or adjusted under 35 U.S.C. 154(b) by 275 days.

(21) Appl. No.: 15/521,604

(22) PCT Filed: Oct. 21, 2015

(86) PCT No.: PCT/KR2015/011147
§ 371 (c)(1),
(2) Date: Apr. 24, 2017

(87) PCT Pub. No.: WO2016/064188
PCT Pub. Date: Apr. 28, 2016

(65) Prior Publication Data
US 2017/0241942 A1   Aug. 24, 2017

(30) Foreign Application Priority Data

Oct. 24, 2014 (KR) .................. 10-2014-0144793
Oct. 24, 2014 (KR) .................. 10-2014-0145552
Oct. 24, 2014 (KR) .................. 10-2014-0145554

(51) Int. Cl.
*G01N 27/407* (2006.01)
*F01N 11/00* (2006.01)
(Continued)

(52) U.S. Cl.
CPC ......... *G01N 27/4077* (2013.01); *C04B 35/48* (2013.01); *C04B 35/6261* (2013.01);
(Continued)

(58) Field of Classification Search
None
See application file for complete search history.

(56) References Cited

U.S. PATENT DOCUMENTS

2007/0215469 A1* 9/2007 Imamura ............ G01N 27/4075
204/424
2013/0341206 A1   12/2013 Schenk et al.

FOREIGN PATENT DOCUMENTS

JP  2002-286680 A  10/2002
JP  2007-248351 A   9/2007
(Continued)

OTHER PUBLICATIONS

International Search Authority/KR, International Search Report dated Feb. 19, 2016 in International Patent Application No. PCT/KR2015/011147 (with English translation), 4 pages.

*Primary Examiner* — Luan V Van
*Assistant Examiner* — Steven E Rosenwald
(74) *Attorney, Agent, or Firm* — Masuvalley & Partners

(57) ABSTRACT

Provided is a method of manufacturing a porous protective layer for a gas sensor. The porous protective layer according to one Example of the present invention is manufactured by a method of manufacturing a porous protective layer for a gas sensor including (1) a step of introducing a composition for forming a porous protective layer including a pore former and aceramic powder, which includes particles having a degree of deformation of 1.5 or more expressed by the following Relational Formula 1 according to the present
(Continued)

invention, onto a sensing electrode for a gas sensor, and (2) a step of sintering the introduced composition for forming a porous protective layer.

8 Claims, 11 Drawing Sheets

(51) Int. Cl.
    *G01N 27/12*     (2006.01)
    *G01N 27/26*     (2006.01)
    *C04B 35/48*     (2006.01)
    *C04B 35/622*     (2006.01)
    *C04B 35/626*     (2006.01)
    *C04B 35/634*     (2006.01)
    *C04B 35/64*     (2006.01)
    *C04B 38/06*     (2006.01)
    *G01N 27/406*     (2006.01)

(52) U.S. Cl.
    CPC .... *C04B 35/62222* (2013.01); *C04B 35/6342* (2013.01); *C04B 35/64* (2013.01); *C04B 38/067* (2013.01); *C04B 38/068* (2013.01); *F01N 11/00* (2013.01); *G01N 27/12* (2013.01); *G01N 27/26* (2013.01); *G01N 27/4067* (2013.01); *C04B 2235/3225* (2013.01); *C04B 2235/3244* (2013.01); *C04B 2235/3246* (2013.01); *C04B 2235/5436* (2013.01); *C04B 2235/6567* (2013.01); *F01N 2560/00* (2013.01); *Y02T 10/47* (2013.01)

(56) References Cited

FOREIGN PATENT DOCUMENTS

| | | | | |
|---|---|---|---|---|
| JP | 2009-080100 A | 4/2009 | | |
| JP | 2011-510280 A | 3/2011 | | |
| JP | 2011-214848 A | 10/2011 | | |
| JP | 2011-214853 | * 10/2011 | .......... | G01N 27/409 |
| JP | 2011-214853 A | 10/2011 | | |
| JP | 2012-093330 A | 5/2012 | | |
| JP | 2013-096792 A | 5/2013 | | |
| KR | 10-2007-0066859 A | 6/2007 | | |
| KR | 101230141 | * 2/2013 | ......... | B01D 67/0041 |
| KR | 10-2016-0049188 A | 5/2016 | | |
| KR | 10-2016-0049189 A | 5/2016 | | |
| WO | 2013/123137 A1 | 8/2013 | | |

\* cited by examiner

# POROUS PROTECTIVE LAYER FOR GAS SENSOR, METHOD FOR PRODUCING SAME, AND GAS SENSOR COMPRISING SAME

CROSS-REFERENCE TO RELATED APPLICATIONS

This application is a U.S. National Phase application under 35 U.S.C. § 371 of International Patent Application No. PCT/KR2015/011147 filed Oct. 21, 2015, which claims priority to Korean Patent Application No. 10-2014-0144793 filed Oct. 24, 2014, Korean Patent Application No. 10-2014-0145552 filed Oct. 24, 2014 and Korean Patent Application No. 10-2014-0145554 filed Oct. 24, 2014, which are hereby expressly incorporated by reference in their entirety.

BACKGROUND

1. Field of the Invention

The present invention relates to a gas sensor, and more particularly, to a porous protective layer for a gas sensor, which is formed on a surface of a gas sensor, a method of manufacturing the same, and a gas sensor including the porous protective layer.

2. Discussion of Related Art

Due to air pollution, environmental pollution, and stability issues of industrial fields, which are caused by industrial development, the necessity of gas sensors for sensing various harmful environmental gas species (e.g., $H_2S$, $H_2$, CO, nitrogen oxides ($NO_x$), sulfur oxides ($SO_x$), $NH_3$, volatile organic compounds (VOCs), etc.) is increasing. Among the gas species, $H_2S$ is a gas contained in bad smell such as bad smell, bad breath, and the like, and should necessarily be measured to purify an environment and establish a pleasant living environment. Also, CO is a gas that is contained in an exhaust gas of gasoline vehicles, sooty smoke discharged from industrial fields, or the like, and should be measured to prevent environmental pollution and maintain a pleasant interior environment of vehicles by adjusting an amount of emission of vehicles driving on roads and adjusting CO gas inflow into an interior of a following vehicle. Specifically, gas sensors capable of measuring oxygen, hydrogen, carbon monoxide, carbon dioxide, $NO_x$, and the like are widely used for detecting a specific gas component in an exhaust gas or measuring the concentration thereof in an internal-combustion engine or the like.

Generally, a porous protective layer is formed on a surface of a gas sensor. The porous protective layer may protect the gas sensor not only from the above-described liquid materials and poisonous materials but also from external impacts, and may be made of a porous material so that the gas sensor may sense a measuring gas. In Japanese Registration Patent No. 4691095 in the related art, a sensor element for measuring physical characteristics of a measuring gas is disclosed.

However, in the related art, there is a problem in that a porous protective layer formed on a gas sensor does not completely block liquid materials, cracks are generated in an external sensing electrode due to thermal shock caused by a temperature difference between the liquid materials and the gas sensor, or materials other than a test gas to be inspected also directly reach the gas sensor due to separation of the porous protective layer from the gas sensor, cracks, or pore collapse. Also, there is a problem in that poisonous materials are easily deposited on the porous protective layer, a response speed of the gas sensor to a measuring gas is lowered, and a concentration of the measuring gas may not be accurately measured.

SUMMARY OF THE INVENTION

The present invention is directed to a porous protective layer for a gas sensor that is capable of protecting a gas sensor from an external impact and a liquid material, protecting the gas sensor from an external physical impact and external physical and chemical factors such as a liquid material and a poisonous material in a test gas, preventing an output of the gas sensor due to an external factor from being reduced, and measuring a concentration of a target gas further rapidly and accurately, and a method of manufacturing the same.

Also, the present invention is directed to a gas sensor that is capable of measuring a concentration of a target gas more rapidly and accurately and includes a porous protective layer having significantly high durability.

According to an aspect of the present invention, there is provided a method of manufacturing a porous protective layer for a gas sensor, wherein the method includes (1) a step of introducing a composition for forming a porous protective layer including a pore former and a ceramic powder, which includes particles having a degree of deformation of 1.5 or more expressed by the following Relational Formula 1, onto a sensing electrode for a gas sensor, and (2) a step of sintering the introduced composition for forming a porous protective layer.

$$\text{degree of deformation} = \frac{\text{diameter of circumscribed circle of cross section of ceramic powder } (\mu m)}{\text{diameter of inscribed circle of cross section of ceramic powder } (\mu m)} \quad \text{[Relational Formula 1]}$$

The ceramic powder may include at least one particle selected from the group consisting of $Al_2O_3$, $SiO_2$, $TiO_2$, $ZrO_2$, AlN, $Si_3N_4$, $Ti_3N_4$, $Zr_3N_4$, $Al_4C_3$, SiC, TiC, ZrC, AlB, $Si_3B_4$, $Ti_3B_4$, $Zr_3B_4$, $3Al_2O_3 \cdot SiO_2$, and $MgAl_2O_4$.

In step 1, the degree of deformation of the ceramic powder may range from 1.8 to 4.2. A ceramic powder which satisfies a condition of the degree of deformation among ceramic powders in step 1 may make-up 50 wt % or more of the entire ceramic powder. The ceramic powders in step 1 may include a first ceramic powder having a degree of deformation which ranges from 1.5 to 2.0 and a second ceramic powder having a degree of deformation which ranges from 3.0 to 4.2, and a weight ratio of the first ceramic powder to the second ceramic powder ranges from 1:1.6 to 1:3.0.

A cross sectional shape of the ceramic powder which satisfies the condition of the degree of deformation may have at least one of a polygonal shape, a star shape, a homed shape, a shape of a letter, an elliptical shape, a dumbbell shape, a roly-poly shape, a cross shape, and a groove shape.

The pore former may include a polymer of monomers selected from the group consisting of radical polymerizable monomers, multifunctional crosslinking monomers, and combinations thereof, a microemulsion polymer bead of monomers selected from the group consisting of radical polymerizable monomers, multifunctional crosslinking monomers, and combinations thereof, an oxide selected from the group consisting of silicon dioxide (SiO$_2$), titanium dioxide (TiO$_2$), and combinations thereof, a carbide selected from the group consisting of carbon, carbohydrates, and combinations thereof, and at least one selected from the group consisting of a mixture thereof.

A sintering temperature in step 2 may range from 800 to 1,700° C.

According to another aspect of the present invention, there is provided a porous protective layer for a gas sensor, which includes ceramic powders having a degree of deformation of 1.5 or more expressed by the following Relational Formula 1, wherein the porous protective layer is formed by welding at least one region of each particles of the ceramic powder to another particle of the ceramic powder.

$$\text{degree of deformation} = \frac{\text{diameter of circumscribed circle of cross section of ceramic powder (µm)}}{\text{diameter of inscribed circle of cross section of ceramic powder (µm)}}$$ [Relational Formula 1]

Also, the porous protective layer may include a first surface facing one surface of an external electrode of the gas sensor and a second surface opposite to the first surface, and may have a diameter gradient having a pore diameter which increases from the second surface to the first surface. In this case, a ratio of an average diameter of pores included in the second surface of the porous protective layer to an average diameter of pores included in the first surface may range from 1:1.8 to 1:6. Also, the average diameter of pores included in the second surface may range from 5.5 to 8 µm and pores having a pore diameter of ±2 µm of the average diameter may make-up 80% or more of all of the pores included in the second surface.

According to still another aspect of the present invention, there is provided a method of manufacturing a porous protective layer for a gas sensor, wherein the method includes (A) a step of introducing a composition for forming a porous protective layer including a ceramic powder and a continuous pore former onto a sensing electrode for a gas sensor and (B) a step of sintering the introduced composition for forming a porous protective layer.

The continuous pore former may be an amphiphilic block copolymer. In this case, the composition for forming a porous protective layer may further include a pore support. In the composition for forming a porous protective layer, a ratio of a gross weight of the ceramic powder and the pore support to a weight of the amphiphilic block copolymer may range from 1:3 to 1:6. The pore support may include at least one of a silicon alkoxide and a glass silicate. The method may further include a step of removing the pore support from the porous protective layer after step B when the composition for forming a porous protective layer further includes the pore support. A weight-average molecular weight of the amphiphilic block copolymer may range from 10,000 to 100,000, and a weight ratio of a hydrophilic block to a hydrophobic block may range from 1:0.6 to 1:19.

According to yet another aspect of the present invention, there is provided a method of manufacturing a porous protective layer for a gas sensor, wherein the method includes (I) a step of introducing a composition for forming a porous protective layer including a ceramic powder and a through pore former onto a sensing electrode for a gas sensor, and (II) a step of sintering the introduced composition for forming a porous protective layer.

The through pore former may be a low melting point staple fiber, and the method may further include a step of forming through pores by the low melting point staple fiber in the composition for forming a porous protective layer being broken-down between steps I and II. Thermal processing may be performed on the composition for forming a porous protective layer at a temperature which ranges from 200 to 400° C. to break-down the low melting point staple fiber.

According to yet another aspect of the present invention, there is provided a porous protective layer for a gas sensor, which protects a sensing electrode of a gas sensor, wherein the porous protective layer for a gas sensor includes through pores passing through a first surface facing a sensing electrode and a second surface opposite to the first surface.

The through pore may have a diameter which increases from the second surface of the porous protective layer to the first surface. In this case, in the through pores, a ratio of the diameter of the second surface of the porous protective layer to the diameter of the first surface may range from 1:1.8 to 1:6.

According to yet another aspect of the present invention, there is provided an electrode for a gas sensor including the porous protective layer for a gas sensor according to the present invention. A thickness of the porous protective layer may range from 20 to 200 µm.

According to yet another aspect of the present invention, there is provided a gas sensor including the electrode for a gas sensor according to the present invention as an external sensing electrode.

In the description of one exemplary embodiment of the present invention, a shape in which a layer is stacked on a layer includes both a shape in which a layer is directly stacked on a layer and a shape in which a layer is indirectly stacked on a layer. For example, a shape in which a first layer is stacked on a second layer includes both of a directly stacked shape in which a third layer is not interposed between the first layer and the second layer and an indirectly stacked shape in which the third layer is interposed between the first layer and the second layer.

In the description of one exemplary embodiment of the present invention, a through pore refers to a pore passing through one surface of a porous protective layer to the other surface opposite to the one surface, and includes reference to both a case in which pores overlap and are continuously formed to become a through pore and a case in which pores are integrally formed at one time.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
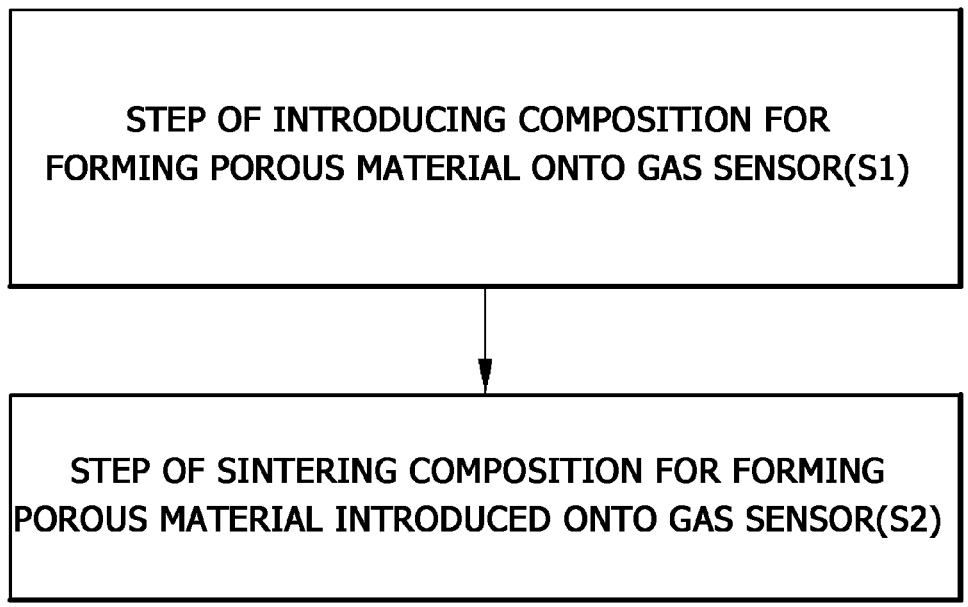
FIG. 1 is a flow chart of a process of manufacturing a porous protective layer according to one exemplary embodiment of the present invention.

Hereinafter, exemplary embodiments of the present invention that are easily performed by those skilled in the art will be described in detail with reference to the accompanying drawings. The embodiments of the present invention may be implemented in several different forms, and are not limited to the embodiments described herein. Portions irrelevant to the description are omitted in the drawings in order to clearly explain the embodiments of the present invention. The same or similar components are denoted by similar reference numerals throughout this specification.

A porous protective layer for a gas sensor according to one embodiment of the present invention is manufactured by a method of manufacturing a porous protective layer for a gas sensor including (1) a step of introducing a composition for forming a porous protective layer, which includes a pore former and a ceramic powder including particles having a degree of deformation of 1.5 or more expressed by the following Relational Formula 1, onto a sensing electrode for a gas sensor and (2) a step of sintering the introduced composition for forming a porous protective layer.

Specifically, FIG. 1 is a flow chart of a process of manufacturing the porous protective layer according to one exemplary embodiment of the present invention. Step S1 of introducing a composition for forming a porous protective layer, which includes a ceramic powder and a pore former, onto the gas sensor, and more specifically, onto a sensing electrode of the gas sensor, is performed as step 1, and step S2 of sintering the composition for forming a porous protective layer introduced onto the gas sensor is then performed as step 2.

The composition for forming a porous protective layer includes a ceramic powder serving as a base material of a porous protective layer and a pore former for forming pores of a porous protective layer.

The ceramic powder may be a material serving as a conventional base material of the porous protective layer for a gas sensor and may protect the gas sensor from external physical and chemical factors. Any ceramic powder may be used without limitation as long as it is for pores to be easily formed therewith. The ceramic powder may preferably include at least one particle selected from the group consisting of $Al_2O_3$, $SiO_2$, $TiO_2$, $ZrO_2$, $AlN$, $Si_3N_4$, $Ti_3N_4$, $Zr_3N_4$, $Al_4C_3$, $SiC$, $TiC$, $ZrC$, $AlB$, $Si_3B_4$, $Ti_3B_4$, $Zr_3B_4$, $3Al_2O_3 \cdot 2SiO_2$, and $MgAl_2O_4$, may more preferably include, at least one of alumina, zirconia, and yttrium oxide, and may furthermore preferably include, yttrium stabilized zirconia.

The ceramic powder may more easily implement pores having a desired diameter and a desired pore dispersion, pores of the manufactured porous protective layer do not collapse even under strong physical impacts, cracks are not generated in the porous protective layer due to an increase in bonding points or bonding surfaces of ceramic powders, and a degree of deformation, which is expressed by the following Relational Formula 1, is 1.5 or more in order to improve an adhesive force of the porous protective layer and to prevent the porous protective layer from being separated from the gas sensor by increasing a surface roughness of the porous protective layer facing the gas sensor, preferably, facing an external sensor of an electrode of the gas sensor.

[Relational Formula 1]
$$\text{degree of deformation} = \frac{\text{diameter of circumscribed circle of cross section of ceramic powder (µm)}}{\text{diameter of inscribed circle of cross section of ceramic powder (µm)}}$$

Figure 2:
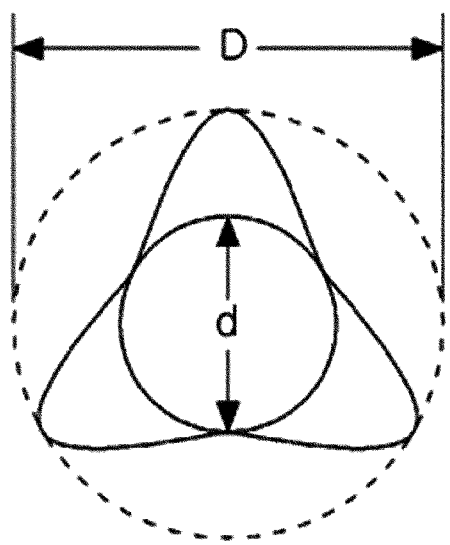
FIG. 2 is a cross-sectional view of a ceramic powder included in one exemplary embodiment of the present invention.

Specifically, FIG. 2 is a cross-sectional view of the ceramic powder included in one exemplary embodiment of the present invention. The degree of deformation of the above Relational Formula 1 refers to a ratio of a diameter D of a circumscribed circle of a cross section of the ceramic powder of FIG. 2 to a diameter d of an inscribed circle thereof. When the degree of deformation is less than 1.5, it may be difficult to implement porosity and a pore diameter by which a test gas may rapidly move and reach a surface of the gas sensor, and it may be difficult to implement desired physical properties due to a problem in that pores may be collapsed by an external physical stimulus or cracks may be generated in the porous protective layer itself.

Figure 3:
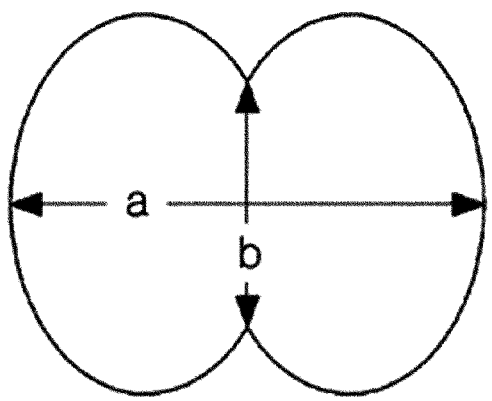
FIG. 3 is a cross-sectional view of a ceramic powder having an intersecting circular cross section according to one exemplary embodiment of the present invention.
Figure 4:
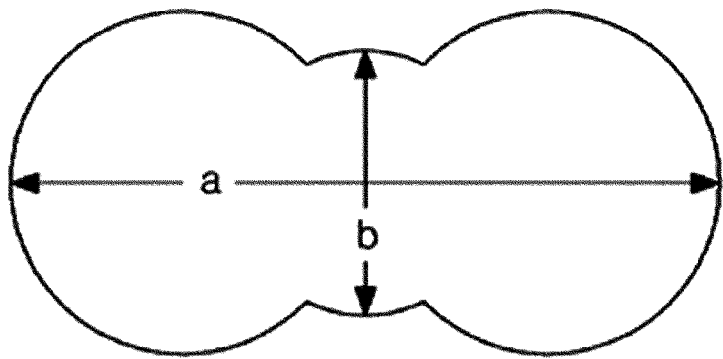
FIG. 4 is a cross-sectional view of a ceramic powder having a dumbbell-shaped cross section according to one exemplary embodiment of the present invention.
Figure 5:
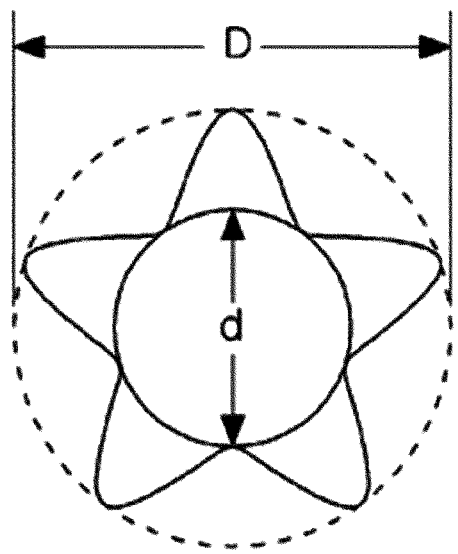
FIG. 5 is a cross-sectional view of a ceramic powder having a five-leaf-shaped cross section according to one exemplary embodiment of the present invention.
Figure 6:
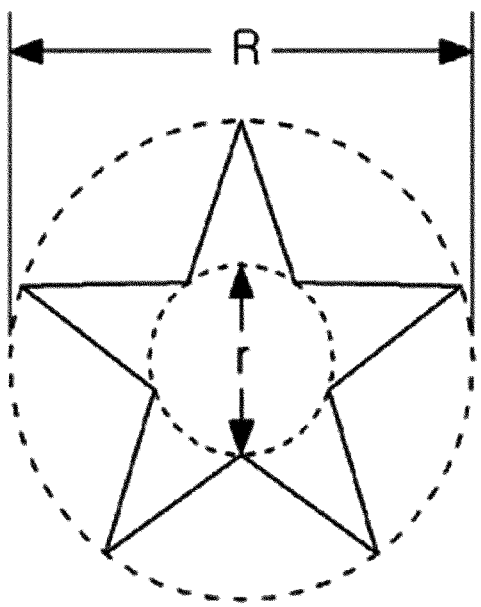
FIG. 6 is a cross-sectional view of a ceramic powder having a star-shaped cross section according to one exemplary embodiment of the present invention.
Figure 7:
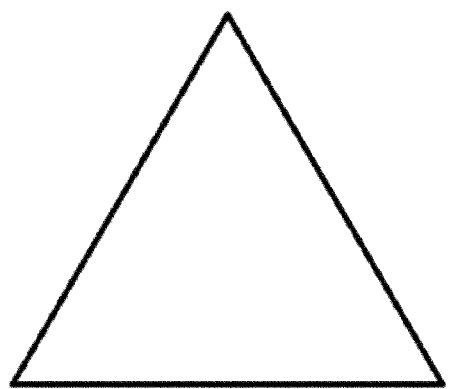
FIG. 7 is a cross-sectional view of a ceramic powder having a triangular cross section according to one exemplary embodiment of the present invention.
Figure 8:
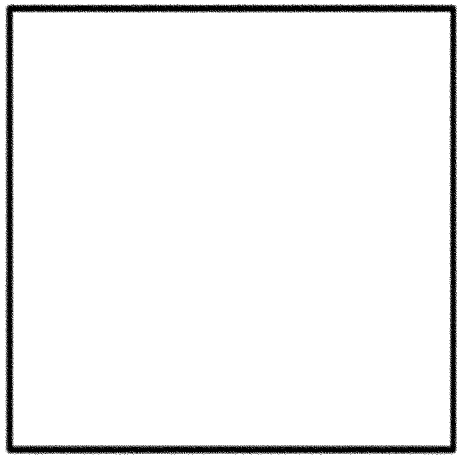
FIG. 8 is a cross-sectional view of a ceramic powder having a tetragonal cross section according to one exemplary embodiment of the present invention.
Figure 9:
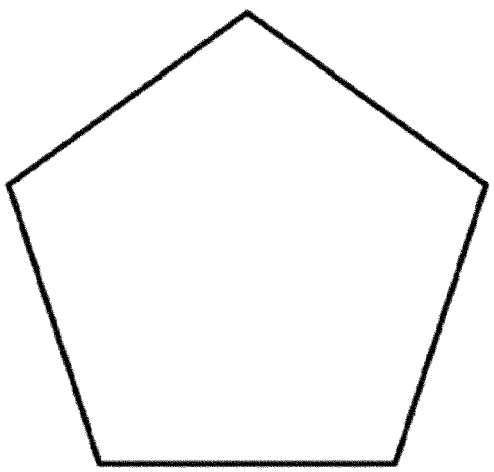
FIG. 9 is a cross-sectional view of a ceramic powder having a pentagonal cross section according to one exemplary embodiment of the present invention.

Meanwhile, in order for the ceramic powder included in one embodiment of the present invention to be implemented as a porous protective layer having further excellent physical properties, at least 50 wt % of the ceramic powder of the composition for forming a porous protective layer, more preferably at least 70 wt % thereof, furthermore preferably at least 85 wt % thereof, and most preferably at least 95 wt % thereof, may be a ceramic powder that satisfies a condition of the degree of deformation of the above Relational Formula 1. When the ceramic powder that satisfies the condition of the degree of deformation of Relational Formula 1 make-up less than 50 wt % of the entire ceramic powder, there is a problem in that it is difficult to implement a desired porosity and pore diameter through the ceramic powder having the degree of deformation, the pores are collapsed by an external physical stimulus, or cracks are generated in the porous protective layer itself. Also, a degree of deformation of the ceramic powder for implementing further improved physical properties may range from 1.8 to 4.2. When the degree of deformation of the ceramic powder is more than 4.2, there may be a problem in that a roughness of one surface of the porous protective layer facing one surface of the gas sensor, preferably facing one surface of an external sensing electrode of the gas sensor, may be significantly increased, an outer surface of the gas sensor which comes into contact with a test gas to measure the presence of a target gas and a concentration of the target gas may be physically damaged, performance of the gas sensor may be degraded, and the porous protective layer may be separated from the gas sensor due to the increased roughness. A cross-sectional shape of the ceramic powder which satisfies the condition of the degree of deformation of the above Relational Formula 1 may include any shape as long as the degree of deformation thereof is 1.5 or more, and there is no limitation on the specific shape thereof. The cross-sectional shape of the ceramic powder which satisfies the condition of the degree of deformation may preferably have at least one of a polygonal shape, a star shape, a horned shape, a shape of a letter, an elliptical shape, a dumbbell shape, a roly-poly shape, a cross shape, and a groove shape. Also, the shape of a letter may include a C shape, an E shape, an F shape, an H shape, an L shape, an S shape, a T shape, a U shape, or a W shape, but the present invention is not limited thereto. Specifically, FIG. 3 is a cross-sectional view of a metal powder having an intersecting circular cross section, and the metal powder has a cross-sectional shape in which two circles are cross-linked to each other. In this case, a major axis length a of the crossed circle becomes a diameter of a circumscribed circle and a minor axis length b thereof becomes a diameter of an inscribed circle. FIG. 4 is a cross-sectional view of a metal powder having a dumbbell shape, and a major axis length of a dumbbell becomes a diameter of a circumscribed circle and a minor axis length b thereof becomes a diameter of an inscribed circle. FIG. 5 is a cross-sectional view of a metal powder having a five-leaf shape, and a length d becomes a diameter of an inscribed circle and a length D becomes a diameter of a circumscribed circle. FIG. 6 is a cross-sectional view of a metal powder having a star shape, and a length r becomes a diameter of an inscribed circle and a length R becomes a diameter of a circumscribed circle. A cross section of a metal powder in FIG. 7 has a triangular shape, a cross section of a metal powder in FIG. 8 has a tetragonal shape, a cross section of a metal powder in FIG. 9 has a pentagonal shape, and a cross section of a metal powder in FIG. 10 has a hexagonal shape.

Figure 10:
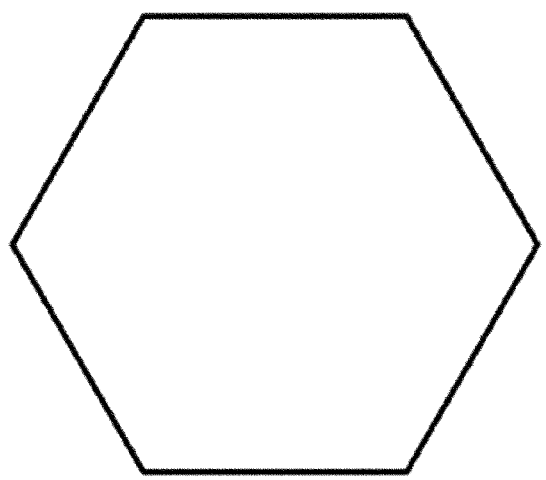
FIG. 10 is a cross-sectional view of a ceramic powder having a hexagonal cross section according to one exemplary embodiment of the present invention.
Figure 11:
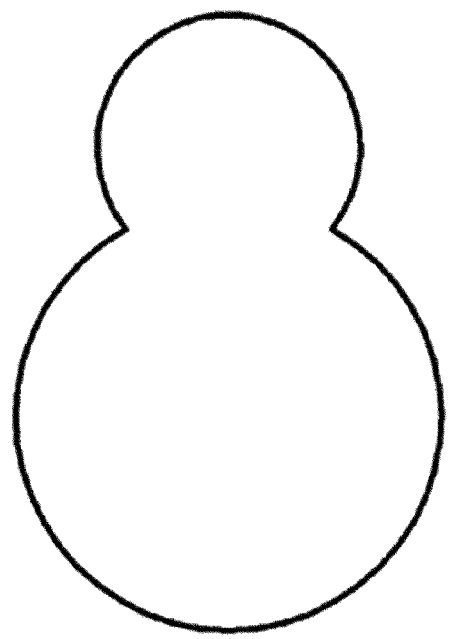
FIG. 11 is a cross-sectional view of a ceramic powder having a roly-poly-shaped cross section according to one exemplary embodiment of the present invention.
Figure 12:
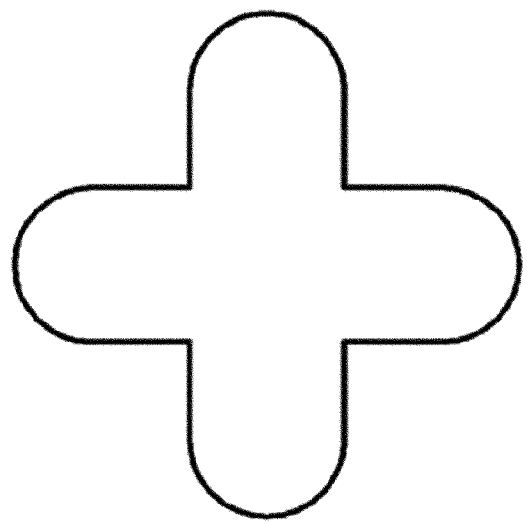
FIG. 12 is a cross-sectional view of a ceramic powder having a cross-shaped cross section according to one exemplary embodiment of the present invention.
Figure 13:
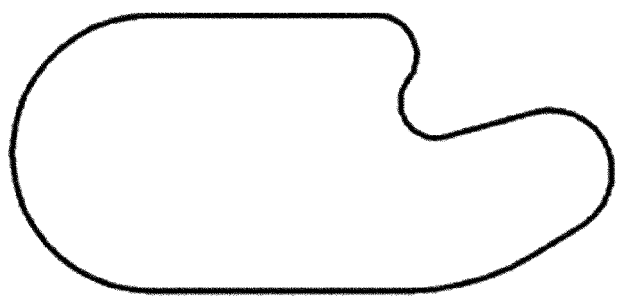
FIG. 13 is a cross-sectional view of a ceramic powder having a dented oval cross section according to one exemplary embodiment of the present invention.
Figure 14:
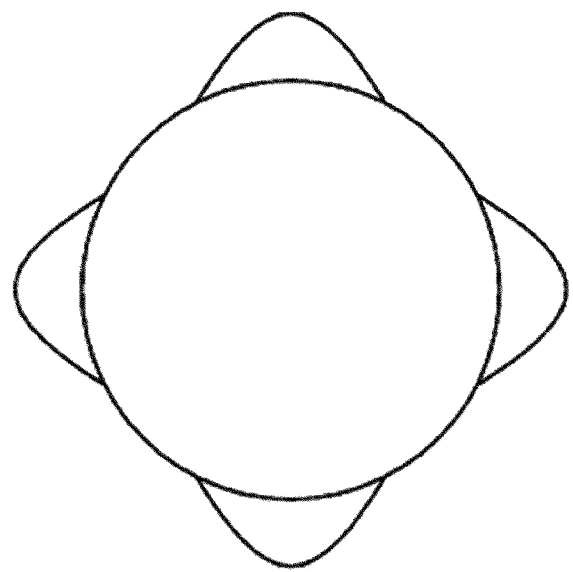
FIG. 14 is a cross-sectional view of a ceramic powder having a grooved cross section according to one exemplary embodiment of the present invention.

A cross section of a metal powder in FIG. 11 has a roly-poly shape, and a cross section of a metal powder in FIG. 12 has a cross shape. A cross section of a metal powder in FIG. 13 has a dented oval shape, and a cross section of a metal powder in FIG. 14 has a grooved shape. The above-described differently-shaped cross sections of the ceramic powders of FIGS. 2 to 13 are all examples that can be applied to the present invention, and ceramic powders having a shape appropriately modified in a range which satisfies the condition of the above-described shape factors may be used. Among the ceramic powders that have the above-described variety of cross-sectional shapes and satisfy the condition of the degree of deformation according to the present invention, a ceramic powder having a bead shape in which a particle diameter ranges from 1 to 200 µm may be manufactured by a mechanical method using a ball mill. Specifically, a ball of zirconia ($ZrO_2$), steel, and tungsten (W) may be used as the ball mill. A specific manufacturing method of the ball mill, a time condition, and the like may be differently designed according to a desired degree of deformation, and the method may be preferably performed for 1 minute to 10 hours, but the present invention is not limited thereto.

Meanwhile, according to one exemplary embodiment of the present invention, the pore diameter is easily controlled, uniformity of the pore diameter may be ensured, and two types of ceramic powders having different degrees of deformation may be mixed in order to minimize pore collapse while implementing a desired pore dispersion. The mixed ceramic powder may be preferably used so that a weight ratio of a first ceramic powder, which has a degree of deformation which ranges from 1.5 to 2.0, to a second ceramic powder, which has a degree of deformation which ranges from 3.0 to 4.2, ranges from 1:1.6 to 1:3.0. When the ceramic powders having different values of degrees of deformation are mixed as described above, a bonding area between particles may be further increased and physical properties such as mechanical strength may be significantly improved. When the condition of the weight ratio of each particle and the first ceramic powder and the second ceramic powder, which satisfy a range of the above-described degree of deformation, are not satisfied, pore diameters may not be uniformly implemented, and pore collapse may occur frequently, and thus the porous protective layer may be easily damaged by a physical impact.

Next, the pore former included in the composition for forming a porous protective layer in step 1 according to the present invention will be described.

A pore former conventionally used for manufacturing a porous protective layer for a gas sensor may be used as the pore former, and any pore former as long as it is easy for pores to be formed therewith, is easily removed by physical and/or chemical dissolution, and does not affect the ceramic powder may be used without limitation. However, preferably, the pore former may include a polymer of monomers selected from the group consisting of radical polymerizable monomers, multifunctional crosslinking monomers, and combinations thereof, a microemulsion polymer bead of monomers selected from the group consisting of radical polymerizable monomers, multifunctional crosslinking monomers, and combinations thereof, an oxide selected from the group consisting of silicon dioxide ($SiO_2$), titanium dioxide ($TiO_2$), and combinations thereof, a carbide selected from the group consisting of carbon, carbohydrates, and combinations thereof, and at least one selected from the group consisting of a mixture thereof.

As specific examples of the radical polymerizable monomers, aromatic vinyl-based monomers such as styrene, p-methylstyrene, m-methylstyrene, p-ethylstyrene, m-ethylstyrene, p-chlorostyrene, m-chlorostyrene, p-chloromethylstyrene, m-chloromethylstyrene, styrene sulfonic acid, p-t-butoxystyrene, m-t-butoxystyrene, fluorostyrene, alpha-methylstyrene, vinyltoluene, and chlorostyrene, (meth)acrylate monomers such as methyl(meth)acrylate, ethyl(meth)acrylate, butyl(meth)acrylate, octyl(meth)acrylate, stearyl (meth)acrylate, benzyl(meth)acrylate, glycidyl(meth)acrylate, fluoroethyl acrylate, trifluoroethyl methacrylate, pentafluoropropyl methacrylate, fluoroethyl methacrylate, hexafluorobutyl(meth)acrylate, hexafluoroisopropyl methacrylate, perfluoroalkyl acrylate, and octafluorophenyl methacrylate, unsaturated carboxylic acids such as vinyl acetate, vinyl propionate, vinyl butyrate, vinyl ether, allyl butyl ether, allyl glycidyl ether, (meth)acrylic acid, and maleic acid, alkyl(meth)acrylamide, vinyl cyanide monomers such as (meth)acrylonitrile, or a mixture thereof may be included. As a representative example of polymers of the radical polymerizable monomers, polystyrene and polymethyl(meth)acrylate may be included.

The multifunctional crosslinking monomers may include allyl compounds such as divinylbenzene, 1,4-divinyloxybutane, divinyl sulfone, diallyl phthalate, diallyl acrylamide, triallyl(iso)cyanurate, and triallyl trimellitate, hexanediol diacrylate, ethylene glycol dimethacrylate, diethylene glycol methacrylate, triethylene glycol dimethacrylate, trimethylene propane trimethacrylate, 1,3-butanediol methacrylate, 1,6-hexanediol dimethacrylate(meth)acrylate, pentaerythritol tetra(meth)acrylate, pentaerythritol tri(meth)acrylate, pentaerythritol di(meth)acrylate, trimethylol propane, tri (meth)acrylate, allyl(meth)acrylate, dipentaerythritol penta (meth)acrylate, glycerol tri(meth)acrylate, allyl(meth)acrylate, or a mixture thereof.

As specific examples of the carbide, monosaccharides such as graphite, glucose, and galactose, disaccharides such as sucrose, or polysaccharides such as starch and farina may be used, and the carbide may have a specific shape such as particles of powder or fibers.

It is preferable that the pore former is in the form of a particle. When the pore former is in the form of a particle, the pore former has an average particle diameter of 100 nm to 50 μm. In order to form a diameter gradient of pores for each height in the cross section of the porous protective layer, it is preferable that the pore former has at least two types of average particle diameters, and it is more preferable that the pore former has two to four types of average particle diameters. When a pore former having two types of average particle diameters is used, a pore former having a large average particle diameter may form a large-diameter pore, and a pore former having a small average particle diameter may form a small-diameter pore, and thus a diameter gradient for each height of the porous protective layer may be derived. The above-described composition for forming a porous protective layer may include 20 to 60 parts by volume of the pore former with respect to 100 parts by volume of the ceramic powder. When less than 20 parts by volume of the pore former is included therein, it may be difficult to implement the desired porosity. When more than 60 parts by volume of the pore former is included therein, there is a problem in that pores of the manufactured porous protective layer may collapse or mechanical properties thereof may be significantly degraded.

Next, a method of introducing the above-described composition for forming a porous protective layer onto a sensing electrode for a gas sensor will be described.

First, a sensing electrode generally refers to an electrode for detecting a specific test gas in a gas sensor which detects a gas. The sensing electrode may correspond to any sensing electrode included in a conventional gas sensor regardless of the type of gas to be detected (e.g., a sensor for detecting oxygen, a sensor for detecting nitrogen, or the like), and the type of gas sensor classified by a gas detection method (e.g., an electrochemical method (a solution conduction method, an electrostatic discharge method, or a diaphragm electrode method) or an electrical method (e.g., a hydrogen ionization method, a thermal conduction method, a contact combustion method, or a semiconductor method)). Various electrode materials having electrical conductivity may be used as the sensing electrode, and preferably platinum, zirconia, and/or a mixture of platinum and zirconia may be used as a material of the sensing electrode. Also, when the composition for forming a porous protective layer is described as being introduced onto the sensing electrode, the description includes both the meaning of the composition for forming a porous protective layer being introduced to directly face at least one surface of the sensing electrode and the meaning of the composition for forming a porous protective layer being introduced onto another layer formed on at least one surface of the sensing electrode to face the composition.

There is no particular limitation on the method of introducing a composition for forming a porous protective layer onto the sensing electrode. The composition may be applied to have a predetermined thickness or may be printed by a printing method known in the art. Also, the amount of composition to be applied or printed may be changed according to a thickness of a desired porous electrode protective layer, but the present invention is not limited thereto. As a specific example, when a room-temperature vacuum powder spraying method is used for the composition for forming a porous protective layer, a method known in the art may be used. As a non-limiting example, a process in which the composition for forming a porous protective layer is firstly introduced into a powder container, an external sensing electrode or a gas sensor to which an external sensing electrode is attached is then mounted in a deposition chamber, and a carrier gas is supplied from a carrier gas container located inside the powder container may be performed. The carrier gas may be air, oxygen, nitrogen, helium, argon, or the like, but the present invention is not limited thereto. A flow rate of the carrier gas may be adjusted to be 1 L/min or more, and the composition powder inside the powder container may be introduced into the carrier gas to be scattered. The carrier gas into which the composition powder is introduced may be introduced into the deposition chamber. It is preferable to adjust a degree of vacuum of the deposition chamber after the carrier gas is introduced into the deposition chamber so that deposition is smoothly performed, and it is more preferable to maintain a degree of vacuum of 1 to 1.5 Torr.

Also, as a specific example, when the composition for forming a porous protective layer is applied as a liquid to a gas sensor, the composition for forming a porous protective layer may further include a binder component and a solvent. The binder component functions to further improve an adhesive force between the ceramic powders and an adhesive force between a surface of the gas sensor, preferably an external sensing electrode, and the porous protective layer manufactured by step 2, which will be described later. A binder component generally used in the art may be used as the binder component, and the binder component may preferably include at least one of a polyvinyl compound, such as polyvinyl butyral, ethyl cellulose, polyester, epoxy, and terpineol, and fluoride compounds such as polyvinylidene fluoride.

Any solvent may be used without limitation as long as it can disperse the composition for forming a porous protective layer and dissolve the binder component. As a non-limiting example, at least one selected from the group consisting of water, ethanol, isopropyl alcohol, n-propyl alcohol, and butyl alcohol may be included as the solvent, but the present invention is not limited thereto.

The composition for forming a porous protective layer may included the binder component 8 to 26 parts by weight and the solvent 20 to 50 parts by weight of based on 100 parts by weight of the ceramic powder. When less than 8 parts by weight of the binder component is included therein, there may be a problem in that an adhesive force between the gas sensor and the manufactured porous protective layer is degraded and thus the porous protective layer may be separated from the gas sensor, or an adhesive force between the ceramic powders is degraded, and thus the pores of the porous protective layer may collapse and cracks may be easily generated therein. When more than 26 parts by weight of the binder component is included therein, the pores of the porous protective layer may be blocked by the binder component, and thus it may be difficult to implement the desired porosity and pore diameter. When the solvent maintains a viscosity by which the composition for forming a porous protective layer may be applied to have a desired thickness, the content of the solvent may be changed and used.

After the above-described step 1 is performed, sintering of the composition for forming a porous protective layer introduced onto the sensing electrode for a gas sensor may be performed as step 2 according to the present invention. In step 2, the sintering may be preferably performed within a range of 800 to 1,700° C., may more preferably be performed within a range of 1,000 to 1,600° C., and may furthermore preferably be performed within a range of 1,300 to 1,550° C., under an air and/or nitrogen atmosphere. When the sintering is performed at less than 800° C., the pore former is not smoothly removed by heat and it may be difficult to implement the porous protective layer having the desired porosity and pore diameter. When the sintering is performed at more than 1,700° C., there may be a problem in that the gas sensor may be damaged by heat. The sintering may be performed for 20 minutes to 5 hours, but the sintering time is not limited thereto.

Meanwhile, when a specific type of pore former is used, the pore former may not be removed by performing sintering by heat after the above-described step 2 is performed. In this case, the pore former may be chemically dissolved and removed. In this case, a solution of strong acid or strong alkali may be used. Hydrofluoric acid may be used as a representative example of the strong acid and sodium hydroxide and potassium hydroxide may be used as a representative example of the strong alkali, but the present is not limited thereto.

Also, in order to implement a desired pore through a more smooth removal of the pore former, a step of sintering the pore former may be performed between the above-described steps 1 and 2. The sintering of the pore former may be preferably performed within a range of 200 to 600° C., and may more preferably be performed within a range of 300 to 500° C., for 20 minutes to 5 hours.

Meanwhile, according to one exemplary embodiment of the present invention, in order to form a gradient having a pore diameter difference between one surface of the porous protective layer manufactured after the above-described step 2 and the other surface opposite to one surface, surfaces of pores included in the other surface opposite to the one surface of the porous protective layer, which faces the gas sensor, preferably facing the external sensing electrode of the gas sensor, may be coated with a pore modifier. The other surface refers to a portion which is 20% or less a total thickness of the porous protective layer inward from the other surface of the porous protective layer based on the thickness of the porous protective layer including the pore included in the other surface. Specifically, the coating of the pore modifier may be performed by applying a mixed solution including the pore modifier, the binder, and the solvent to one surface of the manufactured porous protective layer or by performing introduction the pore modifier to the pores of the porous protective layer through pressurizing and performing thermal processing after the porous protective layer is dipped into the mixed solution. More specifically, after the mixed solution is applied to a portion of the porous protective layer or the porous protective layer is dipped into the mixed solution, thermal processing may be performed at a temperature which ranges from 800 to 1,700° C. after a pressure within a range of 1.5 to 5 atm is applied for 1 minute to 2 hours. When the temperature of the thermal processing is less than 800° C., the pores of the porous protective layer may not be sufficiently coated with the pore modifier and, when the temperature of the thermal processing is more than 1,700° C., a malfunction of the gas sensor may be caused due to high temperature. A mixing ratio of the mixed solution of the pore modifier, the binder, and the solvent is not limited as long as viscosity sufficient to pass through the pores of the porous protective layer may be maintained, and the content of the pore modifier inside the mixed solution may be changed and adjusted in consideration of a particle diameter of the selected pore modifier and a desired pore diameter of another surface of the porous protective layer. The pore modifier may include at least one ceramic powder selected from the group consisting of alumina, spinel, titanium dioxide, zirconia, yttrium oxide, lithium oxide, calcium oxide, magnesium oxide, cerium oxide, and mullite, and it may be preferable to select and use the same type of particles as the porous protective layer in order to implement further improved mechanical properties. Also, it may be preferable that the pore modifier has a particle diameter smaller than the pore diameter formed at the other surface of the above-described porous protective layer. The diameter of the pore modifier may be selected in consideration of the pore diameter implemented in the porous protective layer, and thus the diameter of the pore modifier is not limited. However, a pore modifier having a pore diameter of 35% or less included in the other surface of the porous protective layer may be preferably used, a pore modifier having a pore diameter of 25% or less may be more preferably used, and a pore modifier having a pore diameter of 10% or less may be furthermore preferably used.

Any binder may be used without limitation as long as it easily binds the selected pore modifier to the surface of the pore. As a non-limiting example, polytetrafluoroethylene, polyvinylidene fluoride, polyvinyl alcohol, epoxy resin, ethylene vinyl acetate, cellulose acetate, etc. may be used alone or in a combination of two or more.

Any solvent may be used without limitation as long as it is suitable for dispersing the pore modifier and dissolving the binder. As a non-limiting example, at least one selected from the group consisting of ethanol, isopropyl alcohol, n-propyl alcohol, and butyl alcohol may be used.

Meanwhile, the present invention includes a ceramic powder having a degree of deformation of 1.5 or more, which is expressed by the following Relational Formula 1, and includes a porous protective layer for a gas sensor formed by at least one region of each particle of the ceramic powder being welded to another particle of the ceramic powder.

$$\text{degree of deformation} = \frac{\text{diameter of circumscribed circle of cross section of ceramic powder (µm)}}{\text{diameter of inscribed circle of cross section of ceramic powder (µm)}}$$ [Relational Formula 1]

Figure 17:
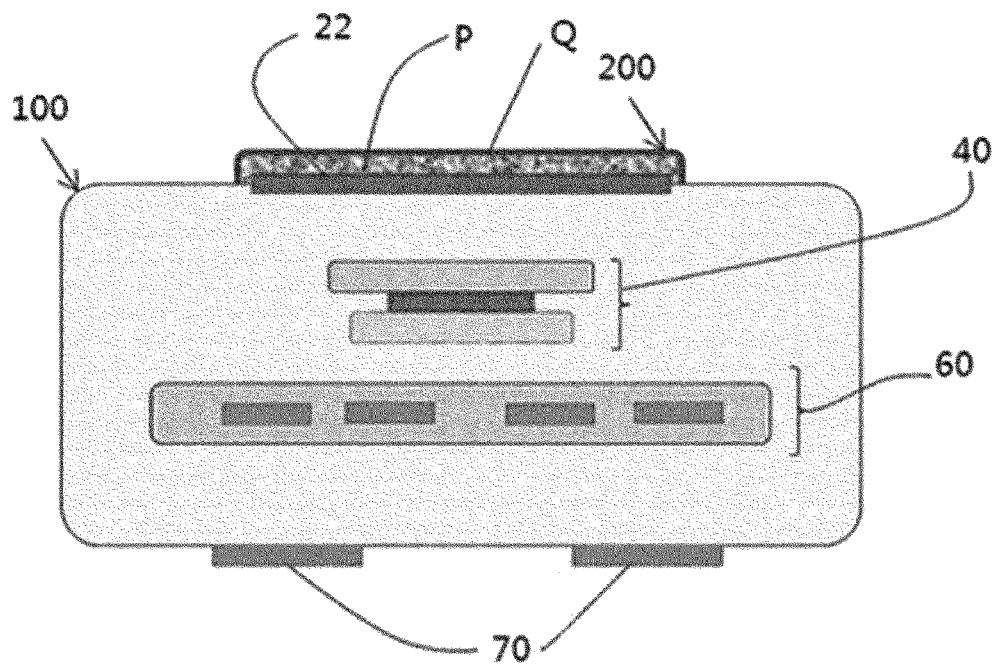
FIG. 17 is a cross-sectional view of a gas sensor according to one exemplary embodiment of the present invention.

Specifically, as illustrated in FIG. 17, in a gas sensor 100 including an external sensing electrode 22, a reference electrode 40, a heater 60, and a tunnel electrode 70, a porous protective layer 200 covers an entire exposed outer surface of the external sensing electrode 22 and includes a first surface P facing an outer surface of the gas sensor 100 and a second surface Q opposite to the first surface P.

Figure 18:
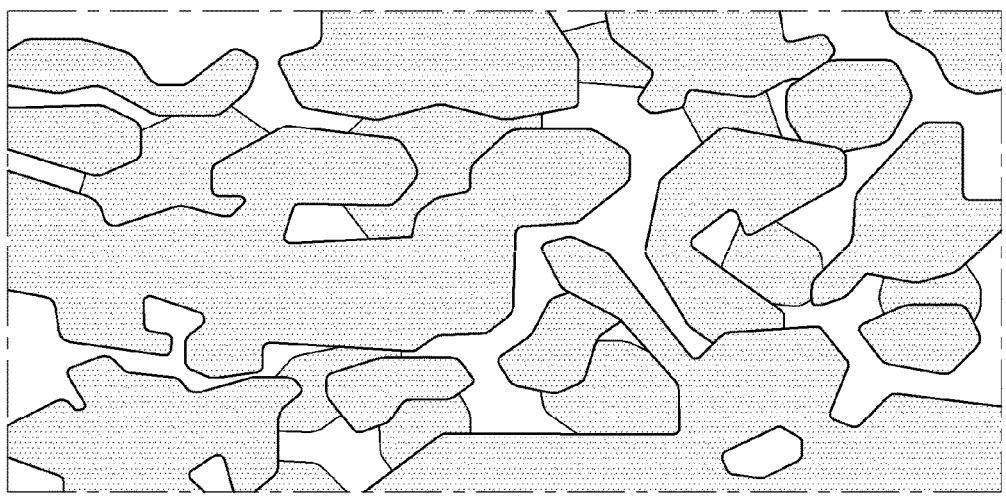
FIG. 18 is a schematic diagram of a cross section of a porous protective layer according to one exemplary embodiment of the present invention.

First, a porous protective layer 200 for a gas sensor according to the present invention includes a ceramic powder having a degree of deformation of 1.5 or more, which is expressed by the following Relational Formula 1, and is formed by at least one region of each particle of the ceramic powder being welded to another particle of the ceramic powder. Specifically, as illustrated in FIG. 18, the porous protective layer may include a ceramic powder having a degree of deformation of 1.5 or more, and at least one region of each particle of the ceramic powder may be melted and bonded to another particle of the ceramic powder. The at least one region of each of the particles may vary according to a shape of the particle, a size of the particle, and a positional relationship between surrounding particles. For example, as illustrated in FIG. 10, when the cross section of the particle has a hexagonal shape, the at least one region of each of the particles may be a surface of the particle or a boundary region in which surfaces of outer surfaces of particles meet, and a volume of the region may vary according to sintering conditions such as a temperature and the like.

The porous protective layer 200 includes a ceramic powder which satisfies the conditions of the degree of deformation according to the present invention. The porous protective layer 200 is formed by melting the at least one region of each of the particles of the ceramic powder and bonding the particle to another particle, and thus a desired pore size and pore dispersion may be more easily implemented. Due to the increase of bonding points or bonding surfaces of the particles of the ceramic powder, pores of the manufactured porous protective layer do not collapse or cracks are not generated even under a strong physical impact. An adhesive force of the porous protective layer may be further improved by increasing roughness of a surface of the porous protective layer facing the gas sensor, and thus the porous protective layer may be prevented from being separated therefrom. Also, in order to implement a porous protective layer having further improved physical properties, the degree of deformation of the ceramic powder may be within a range of 1.8 to 4.2. Also, in order to implement a porous protective layer which exhibits further improved physical properties, a porous protective layer including at least 50% of ceramic particles which satisfy the condition of the degree of deformation according to the present invention may be implemented. Since a critical significance or the like with respect to content of the particle of the ceramic powder, which satisfies the condition of the degree of deformation according to the present invention, is the same as that in the above-described manufacturing method, a description thereof will be omitted. The ceramic powder may be a particle made of a material serving as a base material of a conventional porous protective layer for a gas sensor, and may protect a gas sensor from external physical and chemical factors. Any ceramic powder may be used without limitation as long as it easily forms pores. Any shape of ceramic powder may be used without limitation as long as it satisfies the condition of the degree of deformation in Relational Formula 1. Preferably, at least one of an elliptical shape, a dumbbell shape, a polygonal shape, a star shape, a homed shape, a roly-poly shape, a cross shape, a shape of a letter, and a groove shape may be included.

Meanwhile, the porous protective layer according to one embodiment of the present invention may include two types of ceramic powders having different degrees of deformation, and may preferably include a first ceramic powder having a degree of deformation which ranges from 1.5 to 2.0 and a second ceramic powder having a degree of deformation which ranges from 3.0 to 4.2 with a weight ratio of 1:0.8 to 1:2.5. Accordingly, a dense porous protective layer having a uniform pore diameter and implementing a desired pore dispersion is advantageously implemented, and a porous protective layer having a significantly improved mechanical strength with respect to pore collapse may be implemented.

Also, in the porous protective layer according to one embodiment of the present invention, since pores having a uniform pore diameter are included in one surface of the porous protective layer (e.g., a second surface of the porous protective layer in contact with an atmosphere containing a test gas), an average diameter of the pores included in the second surface of the porous protective layer may range from 5.5 to 8 µm, and the pores having a pore diameter of the average diameter ±2 µm may make up 80% or more of all of the pores included in the second surface. Accordingly, an ability to shield the porous protective layer against poisonous materials, liquids, and the like may be improved, and thus the degradation of performance of the gas sensor may be prevented so that desired physical properties may be more advantageously implemented by the porous protective layer.

Also, in the porous protective layer according to one embodiment of the present invention, a ratio of an average diameter of the pores included in the second surface to an average diameter of pores included in the first surface may be 1.8:6, and may more preferably be 1:2 to 1:4. When the ratio of the average diameters of the pores included in the first surface and the second surface is the above-described ratio, the porous protective layer may sufficiently block penetration of the liquid material into the gas sensor. Since the first surface has a diameter greater than the diameter of the pore of the second surface and imparts a heat insulating property thereto, and damage to the gas sensor caused by liquid materials may be effectively suppressed, a measuring gas may be smoothly supplied to the gas sensor, and thus a concentration of the measuring gas may be more accurately measured.

The porous protective layer 200 may have an average porosity which ranges from 20 to 60% per unit volume, and may preferably have an average porosity which ranges from 30 to 50%. When the average porosity per unit volume of the porous protective layer 200 is less than 20%, gas permeability may be degraded, and it is difficult to perform a supply and/or discharge of a target gas to and/or from the gas sensor, and thus an output of the gas sensor may be degraded. When the average porosity per unit volume of the porous protective layer 200 is more than 60%, there may be a problem in that the mechanical strength of the porous protective layer is significantly lowered, the pores are collapsed, and cracks and separation are generated. Also, the porous protective layer 200 may have an average pore diameter which ranges from 5.95 μm to 42 μm, and preferably which ranges from 16 μm to 32 μm.

Figure 15:
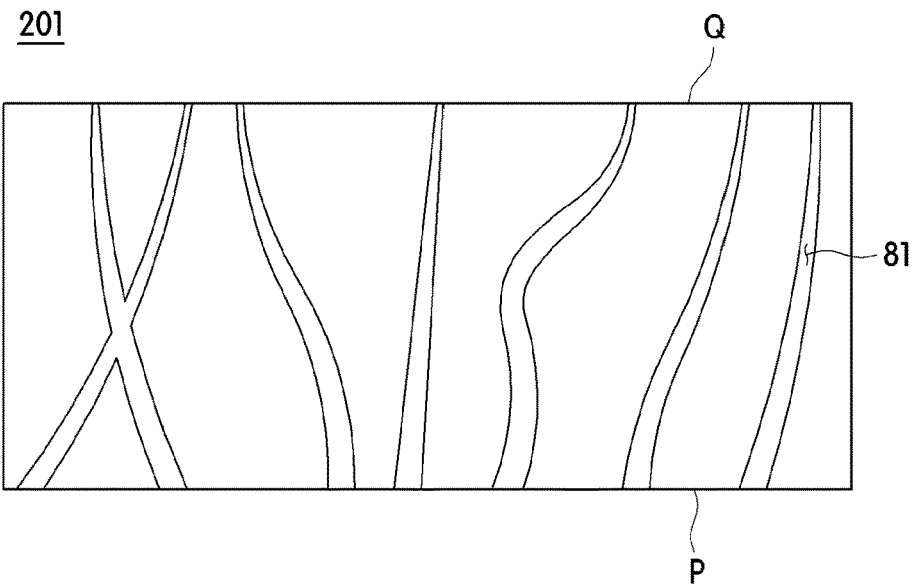
FIG. 15 is a cross-sectional view of a porous protective layer according to one exemplary embodiment of the present invention.

Meanwhile, according to another embodiment of the present invention, referring to FIG. 15, a porous protective layer 201 includes through pores 81 passing through a first surface P facing a sensing electrode and a second surface Q opposite to the first surface P. In this case, the through pores 81 may refer to a structure in which pores are not blocked and are continuous, and the sensing electrode may be an electrode included for sensing a test gas of a gas sensor and may include an external sensing electrode 22.

The porous protective layer 201 for a gas sensor may have gas permeability only in a direction perpendicular to a surface of the sensing electrode so that the through pores 81 pass through the second surface Q and the first surface P, that is, the through pores 81 of the porous protective layer 201 are formed in a direction perpendicular to a surface of the sensing electrode abutting the first surface P. Accordingly, penetration of an exhaust gas, which may penetrate in a direction parallel to the surface of the sensing electrode, may be blocked, an appropriate amount of the target gas may be supplied to the gas sensor while maintaining a diffusion distance of a target gas to be measured in the exhaust gas, and thus the concentration of the target gas may be rapidly and accurately measured.

An average diameter of the through pores 81 may range from 5.5 to 42 μm, may preferably range from 5.95 to 35 μm, and may more preferably range from 16 to 30 μm. When the through pores 81 are formed to have an average diameter which is smaller than 5.5 μm, the gas permeability to the porous protective layer 201 may be lowered, and an output of the gas sensor may be reduced since it is difficult to supply and/or discharge the target gas to and/or from the gas sensor. When the through pores 81 are formed to have an average diameter which is bigger than 42 μm, liquid materials and poisonous materials in the exhaust gas, which may pass through the through pores 81, may penetrate into the porous protective layer 201 and reach the gas sensor, and thus it may be difficult to protect the gas sensor from these materials, and thus it may become difficult to supply an appropriate amount of the target gas to the gas sensor, and to more accurately measure the concentration of the target gas.

Meanwhile, the through pores 81 may have a diameter which increases from the second surface Q of the porous protective layer 201 toward the first surface P. For example, when a diameter of the through pores 81 at the second surface Q is 16 μm, a diameter of the through pores 81 at the first surface P may be 20 μm, which is greater than 16 μm. The reason why the through pores 81 are formed to have the diameter which increases from the second surface Q of the porous protective layer 201 toward the first surface P is as follows.

Primarily, this is because the total volume of the through pores 81 at the first surface P is increased and a heat insulating property is imparted thereto when the diameter of the first surface P is formed to be large. When the heat insulating property is imparted in this way, it is difficult for the gas sensor to be cooled due to the heat insulating property even when the second surface Q is cooled by liquid materials, and thus damage due to the liquid materials may be effectively suppressed. Secondarily, this is because a diffusion speed of gas passing through the porous protective layer 201 is affected by an average porosity per unit volume of the porous protective layer 201 and the diameter of the through pores 81. For example, when the diameter of the through pores 81 is large, a diffusion resistance for diffusing a plurality of gas molecules while the plurality of gas molecules are squeezed into the through pores 81 and collide with each other is reduced, and the diffusion speed is increased. On the other hand, when the diameter of the through pores 81 is small, the diffusion resistance for diffusing gas molecules while the plurality of gas molecules are squeezed into the through pores 81 and collide with each other is reduced, and the diffusion speed is reduced. Therefore, when the diameter of the through pores 81 is increased from the second surface Q of the porous protective layer 201 to the first surface P, porosity of the pores at the first surface P becomes higher than that of the pores of the second surface Q, and a gas diffusion resistance from the second surface Q to the first surface P is greatly reduced. As a result, for the above-described two reasons, the porous protective layer 201 in the present invention may sufficiently block penetration of a liquid material since the diameter of the through pores 81 at the second surface Q is small. Since the diameter of the through pores 81 at the first surface P is large and a heat insulating property is imparted, damage caused by the liquid materials of the gas sensor may be effectively suppressed, and the target gas may be smoothly supplied to the gas sensor, and thus the concentration of the target gas may be more rapidly and accurately measured.

Furthermore, the through pores 81 may have a ratio of the diameter of the second surface Q of the porous protective layer 201 to the diameter of the first surface P that ranges from 1:1.8 to 1:6, and preferably ranges from 1:2.0 to 1:4.0. When the pores at the first surface and the pores at the second surface have such a diameter ratio, the porous protective layer 201 may sufficiently block penetration of a liquid material into the gas sensor. Since the diameter of the through pores 81 at the first surface P is larger than that of the through pores 81 at the second surface Q a heat insulating property is imparted, damage to the gas sensor caused by the liquid materials may be effectively suppressed, and the target gas may be smoothly supplied to the gas sensor.

Meanwhile, the porous protective layer 201, in which the through pores 81 are formed, may have an average porosity per unit volume which ranges from 20 to 60%, and preferably an average porosity per unit volume which ranges from 30 to 50%.

A porous protective layer, in which through pores according to another embodiment of the present invention are formed, is manufactured by a method of manufacturing a porous protective layer for a gas sensor including (I) a step of introducing a composition for forming a porous protective layer including a ceramic powder and a through pore former onto a sensing electrode for a gas sensor and (II) a step of sintering the introduced composition for forming a porous protective layer.

Since the description of the sensing electrode and the composition for forming a porous protective layer including the ceramic powder and the like in step I is the same as that described above, a detailed description thereof will be omitted, and a difference from the above-described manufacturing method will be mainly described.

The through pore former may be a short fiber, and may preferably be a low melting point staple fiber. The low melting point staple fiber may serve as the pore former in the composition. The low melting point staple fiber may be broken-down by heating the composition, and pores may be formed in the portions at which low melting point staple fibers broke-down.

Generally, a resin ball is mainly used as the pore former. When pores are formed using a resin ball, a window between the pores formed through the resin ball may not be formed, and thus the pores may be clogged. Also, a case in which the pores are closed on a surface of the porous protective layer due to a surface tension of a composition including the resin balls may occur. In order to address such a problem, a low melting point staple fiber may be used as the pore former in the present invention.

The low melting point staple fiber may be introduced onto the sensing electrode to pass through a first surface facing the sensing electrode of the porous protective layer and a second surface opposite to the first surface. The low melting point staple fiber introduced in this way may break-down, and through pores passing through the first surface and the second surface of the porous protective layer may be formed.

Also, the low melting point staple fiber may have a fineness which ranges from 0.5 to 5 denier, may preferably have a fineness which ranges from 0.8 to 3 denier, and may more preferably have a fineness which ranges from 1.0 to 2.0 denier. As described above, the through pores are formed by the breaking-down of the low melting point staple fiber. Since the low melting point staple fiber having the above-described fineness is included in the composition, the through pores may have an average diameter which ranges from 5 µm to 40 µm, may preferably have an average diameter which ranges from 5.95 µm to 35.9 µm, and may more preferably have an average diameter which ranges from 16 µm to 24 µm. In other words, when the fineness of the low melting point staple fiber is less than 0.5 denier, the average diameter of the through pore formed by the breaking-down of the low melting point staple fiber may be less than 5 µm, gas permeability of the porous protective layer may be lowered, and an outputs of the gas sensor may be reduced since it is difficult to smoothly supply and/or discharge a target gas to and/or from the gas sensor. When the fineness of the low melting point staple fiber is more than 5 denier, the average diameter of the through pore formed by the breaking-down of the low melting point staple fiber may be more than 40 µm, and liquid materials and poisonous materials in an exhaust gas, which may pass through the through pore, may penetrate into the porous protective layer and may reach the gas sensor, and thus it may be difficult to protect the gas sensor from these materials, and thus it may become difficult to supply an appropriate amount of the target gas to the gas sensor and to more accurately measure the concentration of the target gas.

Meanwhile, the fineness of the low melting point staple fiber may be reduced from one end thereof toward the other end. By using such a low melting point staple fiber, the through pores formed by the breaking-down of the low melting point staple fiber may be formed to have a diameter which is increased from the second surface of the porous protective layer to the first surface.

Specifically, one end of a low melting point staple fiber having high fineness may be located on the first surface of the porous protective layer, and the other end having low fineness may be located on the second surface of the porous protective layer. When the through pores are formed by breaking-down the low melting point staple fiber, the through pores may be formed to have a diameter which increases from the second surface of the porous protective layer to the first surface.

As described above, the reason why the through pores of the porous protective layer of the present invention are formed to have a diameter which increases from the second surface of the porous protective layer to the first surface is that the diameter of the through pore at the second surface is small so that penetration of a liquid material may be sufficiently blocked, the diameter of the through pore at the first surface is large so that a heat insulating property may be imparted to the porous protective layer, damage to the gas sensor caused by liquid materials may be effectively suppressed, and the target gas may be smoothly supplied to the gas sensor, and thus the concentration of the target gas may be more rapidly and accurately measured.

Furthermore, the through pores may have a ratio of the diameter of the second surface of the porous protective layer to the diameter of the first surface which ranges from 1:1.8 to 1:6, and the ratio may preferably range from 1:2.0 to 1:4. When the pores of first surface and the second surface have such a diameter ratio, the porous protective layer may sufficiently block penetration of liquid materials into the gas sensor. Since the diameter of the through pore at the first surface is greater than that of the through pore at the second surface and a heat insulating property may be imparted thereto, damage to the gas sensor caused by the liquid materials may be effectively suppressed, and the target gas may be smoothly supplied to the gas sensor.

Meanwhile, the low melting point staple fiber having a fiber length longer than an average thickness of the porous protective layer may be used. Since through pores passing through the first surface and the second surface of the porous protective layer are formed by sintering the low melting point staple fiber as described above, it may be difficult to form the through pores passing through the first surface and the second surface of the porous protective layer when the fiber length of the low melting point staple fiber is shorter than the average thickness of the porous protective layer. For example, when the average thickness of the porous protective layer is 100 µm, the fiber length of the low melting point staple fiber may be at least 100 µm.

Furthermore, polyester fibers having a melting point which ranges from 70 to 150° C., and preferably having a melting point which ranges from 80 to 120° C., may be used as the low melting point staple fiber. A break-down temperature of the low melting point staple fiber may range from 200 to 400° C., and may preferably range from 300 to 400° C. In this case, when a melting point of the low melting point staple fiber for forming through pores by being broken-down is more than 150° C., incomplete combustion or a pyrolysis reaction occurs in a break-down reaction, and carbonization may occur to generate amorphous carbon. Accordingly, a problem of partially generating the through pores may occur. For example, when the through pores are formed using polyethylene terephthalate (PET) fibers having a melting point which ranges from 250 to 280° C., the PET fibers are carbonized by a partial thermal decomposition reaction to generate amorphous carbon, and thus a smooth flow of a measuring gas into the through pores may be interrupted.

Meanwhile, the low melting point staple fiber 25 to 60 parts by weight of based on 100 parts by weight of a porous-forming body may be included in the composition for forming a porous protective layer. When less than 25 parts by weight of the low melting point staple fiber is included therein, an average porosity per unit volume of the porous protective layer may be decreased, gas permeability thereof may be lowered, and an output of the gas sensor may be reduced since it is difficult to smoothly supply and/or the discharge the target gas to and/or from the gas sensor. When more than 60 parts by weight of the low melting point staple fiber is included therein, it may be difficult to form the porous protective layer.

Also, since description of step II is the same as that in step 2 of the above-described other manufacturing method, a detailed description thereof will be omitted.

Figure 16:
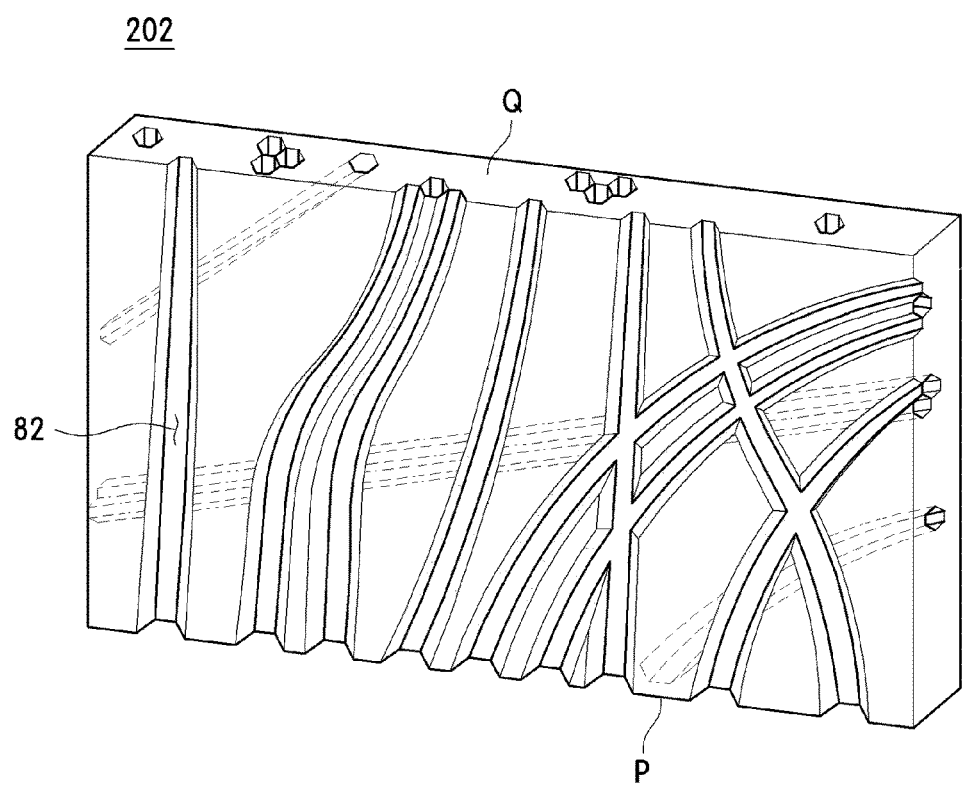
FIG. 16 is a cross-sectional view of a porous protective layer according to one exemplary embodiment of the present invention.

Meanwhile, as illustrated in FIG. 16, a porous protective layer according to still another embodiment of the present invention includes through pores 82 passing through a first surface P facing a sensing electrode (not illustrated) and a second surface Q opposite to the first surface P through continuous pores. In this case, continuous pores refer to a structure in which a plurality of pores are continuously connected to each other. In addition, the continuous pores may be formed in a direction parallel to a gas sensor, and may be designed to have a specific direction. Also, the sensing electrode may be an electrode included for sensing a test gas of the gas sensor, and may include an external sensing electrode (not illustrated).

A porous protective layer 202 for a gas sensor may have a gas permeability only in a direction perpendicular to a surface of the sensing electrode so that the continuous pores 82 pass through the second surface Q and the first surface P, that is, the through pores 82 of the porous protective layer 202 are formed in a direction perpendicular to the surface of the sensing electrode abutting the first surface P. In other words, penetration of an exhaust gas which may penetrate from a direction parallel to the surface of the sensing electrode may be blocked, an appropriate amount of the target gas may be supplied to the gas sensor while maintaining a diffusion distance of a target gas to be measured in the exhaust gas, and thus the concentration of the target gas may be rapidly and accurately measured.

An average diameter of the continuous pore-type through pores 82 may range from 5.5 to 42 μm, may preferably range from 5.95 to 35 μm, and may more preferably range from 16 to 30 μm.

Meanwhile, the continuous pore-type through pores 82 may have a diameter which increases from the second surface Q of the porous protective layer 202 to the first surface P. For example, when diameter of the continuous pore-type through pores 82 at the second surface Q is 16 μm, diameter of the continuous pore-type through pores 82 at the first surface P may be 20 μm, which is greater than 16 μm.

Since the reason why the continuous pore-type through pores 82 is formed to have the diameter which increases from the second surface Q of the porous protective layer 202 to the first surface P is the same as that described above, a description thereof will be omitted.

A ratio of the diameter of the continuous pore-type through pores 82 at the second surface Q of the porous protective layer 202 to the diameter of the continuous pore-type through pores 82 at the first surface P may range from 1:1.8 to 1:6.0, and may preferably range from 1:2.0 to 1:4.0. Also, the porous protective layer 202 may have an average porosity per unit volume which ranges from 20 to 60%, and may preferably have an average porosity which ranges from 30 to 50%.

Meanwhile, the above-described porous protective layer 202 according to still another embodiment of the present invention may be manufactured by a method of manufacturing a porous protective layer for a gas sensor including (A) a step of introducing a composition for forming a porous protective layer including a ceramic powder and a continuous pore former onto a sensing electrode for a gas sensor and (B) a step of sintering the introduced composition for forming a porous protective layer.

Since the description of the composition for forming a porous protective layer including the ceramic powder and the like in step A and the description of step B are the same as those in step 1 and step 2, a difference therebetween will be mainly described below.

The continuous pore former may serve to form pores in the manufactured porous protective layer 202. Since the composition is sintered in step B, which will be described below, the continuous pore former breaks-down and pores may be formed in portions at which the composition broke-down. The pores formed by the continuous pore former may be continuous pores. Here, continuous pores refer to a structure in which a plurality of pores are continuously connected to each other. The continuous pores passing through the first surface facing the sensing electrode and the second surface opposite to the first surface may be formed by the continuous pore former being broken-down. In addition, the continuous pores may be formed in a direction parallel to the gas sensor and may be designed to have a specific direction.

The continuous pore former may be an amphiphilic block copolymer. Generally, a resin ball is mainly used as a pore former. When pores are formed using a resin ball, a window between the pores formed through the resin ball may not be formed, and thus the pores may be clogged. Also, a case in which the pores are closed on the surface of the porous protective layer due to a surface tension of a composition including the resin balls may occur. In order to address such a problem, an amphiphilic block copolymer may be used as the pore former in one embodiment of the present invention.

Since the amphiphilic block copolymer is a copolymer, the amphiphilic block copolymer has a property of being self-assembled as a material having various structures according to relative mass fractions (volume fractions) of hydrophilic and hydrophobic blocks, respectively. In other words, as a fraction of each block is adjusted, the most stable structure is formed thermodynamically in its composition. When a fraction of a hydrophilic portion and fraction of a hydrophobic portion are similar, a lamellar structure may be formed, and various structures may be formed as a fraction of one block increases.

Also, the amphiphilic block copolymer included in one embodiment of the present invention may artificially induce formation of continuous pores by increasing a mass fraction (a volume fraction) of the hydrophilic portion using a precursor, which may be selectively injected only to a hydrophilic portion in order to form a stable structure having continuous pores. As a result, the hydrophilic block of the amphiphilic block copolymer and the precursor may form a matrix, and the hydrophobic block may be self-assembled in the form of pores arrangement into pores to form the continuous pores The amphiphilic block copolymer may have a weight ratio of the hydrophilic block to the hydrophobic block which ranges from 1:0.6 to 1:19, and may preferably have a ratio which ranges from 1:4 to 1:13 to form a stable structure having continuous pores. In this case, the amphiphilic block copolymer may have a weight-average molecular weight which ranges from 10,000 to 100,000, and may preferably have a weight-average molecular weight which ranges from 20,000 to 80,000. When the amphiphilic block copolymer satisfies the weight ratio of the hydrophilic block to the hydrophobic block and the average molecular weight, the amphiphilic block copolymer may be formed to have a stable structure and may satisfy the average porosity per unit volume of the porous protective layer of the present invention.

The amphiphilic block copolymer may be in the form in which the hydrophilic block and the hydrophobic block are covalently bonded. Specifically, the amphiphilic block copolymer may include at least one selected from the group consisting of poly(styrene)-b-poly(acrylamide), poly(styrene)-b-poly(ethylene oxide), poly(styrene)-b-poly(N, N-dimethyl acrylamide), poly(isobutylene)-b-poly(ethylene oxide), poly(isobutylene)-b-poly(4-vinylpyridine), poly(isobutylene)-b-poly(2-vinylpyridine), poly(styrene)-b-poly(bipyridyl methyl acrylate), poly(styrene)-b-poly(lactide), poly(styrene)-b-poly(2-vinylpyridine), poly(styrene)-b-poly(4-vinylpyridine), and preferably poly(styrene)-b-poly(acrylamide) or poly(styrene)-b-poly(ethylene oxide).

Meanwhile, the continuous pore former 300 to 600 parts by weight of based on 100 parts by weight of a porous-forming body may be included in a composition for forming a porous protective layer. When less than 300 parts by weight of the continuous pore former is included therein, an average porosity per unit volume of the porous protective layer may be decreased, gas permeability thereof may be lowered, and an output of gas sensor may be reduced since it is difficult to smoothly supply and/or discharge the target gas to and/or from the gas sensor. When more than 600 parts by weight of the continuous pore former is included therein, it may be difficult to form the porous protective layer.

Meanwhile, when an amphiphilic block copolymer is used as the continuous pores former, a pore support may be further included in the composition for forming a porous protective layer. The pore support may transition to a stable inorganic material when the composition is sintered in step B, and thus mechanical stability and thermal durability of the composition may be improved. Also, the pore support may be uniformly distributed in the composition, and may function to prevent collapse of the pores and a shrinkage phenomenon during the sintering process, and may stably maintain a structure thereof.

Also, the pore support may include at least one of silicon alkoxide and glass silicate, and the silicon alkoxide may include at least one of tetramethyl orthosilicate (TEOS) and aluminosilicate. Also, the pore support 25 to 80 parts by weight of based on 100 parts by weight of the porous-forming body may be included in the composition for forming a porous protective layer. When less than 25 parts by weight of the pore support is included, the pore support may not serve to support the pores during the sintering process. When more than 80 parts by weight of the pore support is included, a problem in that the pores of the continuous pore former are prevented from being formed may occur. Meanwhile, a ratio of a gross weight of the porous-forming body and the pore support to a weight of the continuous pore former may range from 1:3 to 1:6, and may preferably range from 1:4 to 1:5. When the ratio is out of the above ratio, it may be difficult for the continuous pore former to form a stable structure having continuous pores.

Meanwhile, the present invention provides an electrode for a gas sensor including the porous protective layer for a gas sensor according to the present invention.

The electrode may be included in a conventional gas sensor and may be an external sensing electrode of a gas sensor, which comes into contact with a test gas. A shape, thickness, size, and material of the electrode are not limited in the present invention.

A porous protective layer may be formed to cover one surface of the electrode in its entirety, and in this case, a thickness thereof may range from 20 to 200 μm. According to one exemplary embodiment of the present invention, a thickness of the porous protective layer 200 which is formed on at least one surface of the gas sensor 100 may range from 20 to 200 μm, and may preferably range from 50 to 100 μm. That is, liquid materials such as water and/or oil which may cause cracking of the gas sensor may penetrate into pores of the porous protective layer 200. The porous protective layer 200 may be formed on a surface of the gas sensor in the present invention to have a thickness of 20 μm or more, and thus liquid materials may be dispersed before coming into contact with the gas sensor. In other words, when the porous protective layer 200 is formed on the surface of the gas sensor to have a thickness of less than 20 μm, the porous protective layer 200 may not sufficiently protect the gas sensor from an external impact and a liquid material. Also, when the porous protective layer 200 is formed to have a thickness of more than 20 μm, it may be inefficient in terms of a manufacturing cost of the gas sensor, a response speed may be reduced, and thus it may be difficult to more accurately measure a concentration of a measuring gas.

Figure 19:
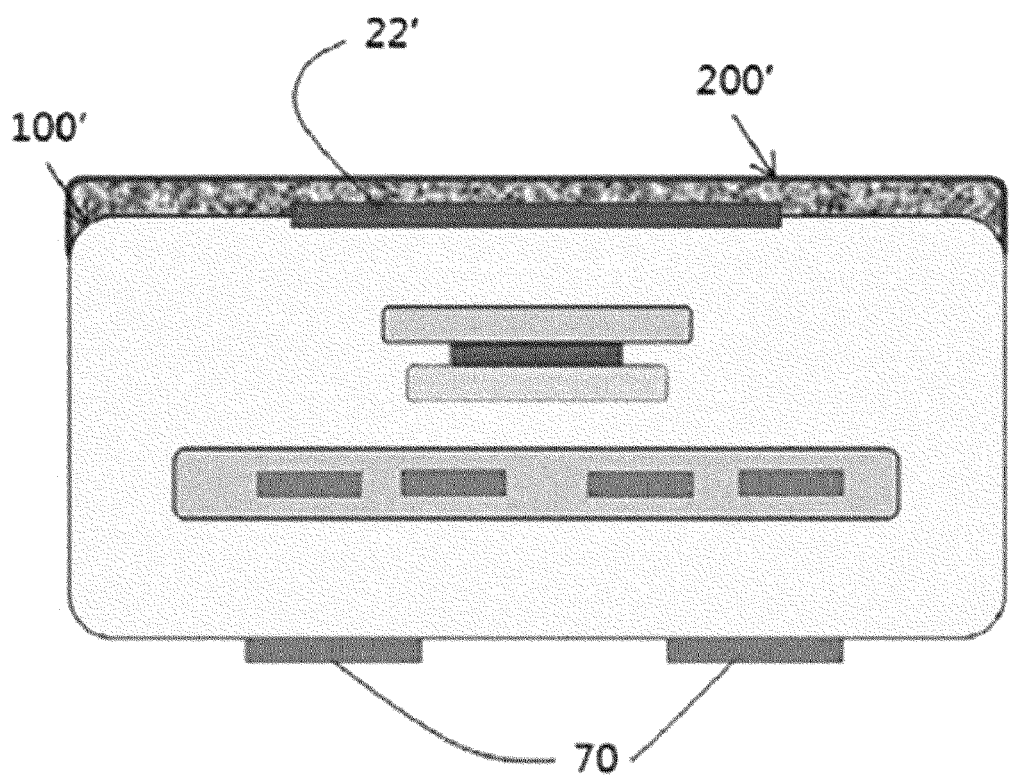
FIG. 19 is a cross-sectional view of a gas sensor according to one exemplary embodiment of the present invention.

Also, the present invention provides a gas sensor including the electrode for a gas sensor according to the present invention. Specifically, as illustrated in FIG. 19, a porous protective layer 200' is formed to cover an entire upper portion of one surface of a gas sensor 100' including an external sensing electrode 22'. Any sensor may be used without limitation as long as it generally detects a gas, and a specific detection method and a structure thereof are not limited in the present invention.

Also, the present invention provides a gas sensor including the porous protective layer according to the present invention.

Any sensor may be used without limitation as long as it generally detects a gas, and a gas detection method is not limited. Preferably, the gas sensor may be a gas sensor which detects a gas by an electrochemical method (a solution conduction method, an electrostatic discharge method, or a diaphragm electrode method) or an electrical method (a hydrogen ionization method, a thermal conduction method, a contact combustion method, or a semiconductor method). Also, a gas to be detected is not limited, and the gas sensor may be a gas sensor for detecting a gas made of at least one of $H_2$, CO, $NO_x$, $SO_x$, $NH_3$, volatile organic compounds (VOCs), C, H, O, and N. Hereinafter, a stacked gas sensor will be described in detail, but the type of the gas sensor is not limited thereto.

Figure 20:
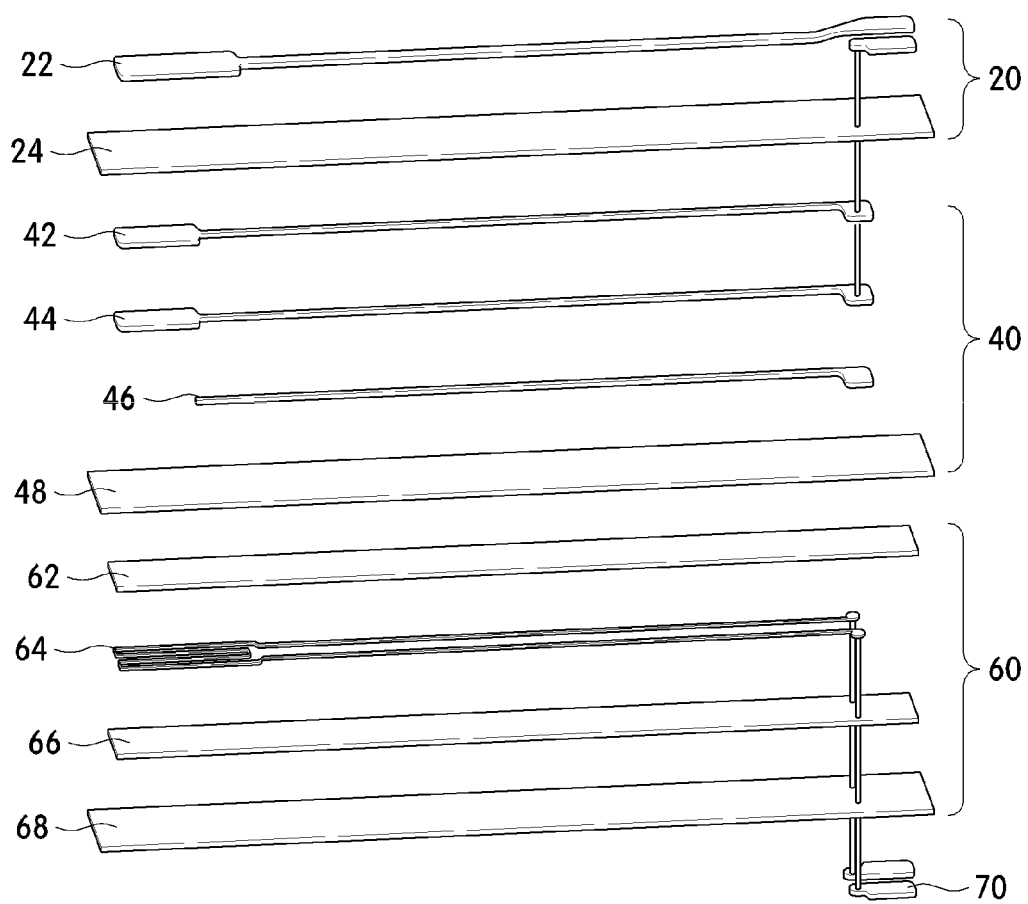
FIG. 20 is an exploded perspective view of a stacked gas sensor according to one exemplary embodiment of the present invention.

Referring to FIG. 20, a gas sensor 100 may include an electrode sensing unit 20, a reference electrode 40, and a heater 60, which are sequentially stacked in order from top to bottom.

The electrode sensing unit 20 may be a portion capable of measuring an electromotive force difference due to a difference between concentrations of a measuring gas, and may include an external sensing electrode 22 and a sensor sheet 24.

The external sensing electrode 22 may be stacked on an uppermost portion of the gas sensor 100 and may oxidize and/or reduce a specific measuring gas. Various electrode materials having electrical conductivity may be used as the external sensing electrode 22, and platinum, zirconia, and/or a mixture of platinum and zirconia may be preferably used as a material of the external sensing electrode 22.

The sensor sheet 24 may be stacked under the external sensing electrode 22 and may move a specific measuring gas which is oxidized and/or reduced by the external sensing electrode 22. Various materials having high-temperature ionic conductivity and high-temperature durability may be used as a material of the sensor sheet 24, and zirconia may be preferably used as the material of the sensor sheet 24.

Also, the reference electrode 40 may be a portion capable of collecting specific measuring gas ions and may include insulating layers 42 and 46, an internal reference electrode 44, and a reference sheet 48. Preferably, the reference electrode 40 may include the insulating layer 42, the internal reference electrode 44, the insulating layer 46, and the reference sheet 48, which are sequentially stacked from top to bottom.

The insulating layers 42 and 46 serve to insulate between a heater electrode 64, which will be described below, and the electrode sensing unit 20. Various insulating materials may be used as a material of the insulating layers 42 and 46, and preferably alumina may be used as the material of the insulating layers 42 and 46.

The internal reference electrode 44 serves to collect specific measuring gas ions. Various electrode materials having electrical conductivity may be used as the internal reference electrode 44, and preferably platinum, zirconia, and/or a mixture of platinum and zirconia may be used as the material of the internal reference electrode 44.

The reference sheet 48 may move heat which is generated in the heater 60. Various materials having thermal conductivity and high-temperature durability may be used as a material of the reference sheet 48, and preferably zirconia may be used as the material of the reference sheet 48.

Also, the heater 60 may be a portion capable of heating the external sensing electrode 22 of the electrode sensing unit 20 to a temperature at which ionic conductivity is achieved, and may include insulating layers 62 and 66, the heater electrode 64, the tunnel sheet 68, and a tunnel electrode 70. Preferably, the heater 60 may include the insulating layer 62, the heater electrode 64, the insulating layer 66, the tunnel sheet 68, and the tunnel electrode 70, which are sequentially stacked from top to bottom.

The insulating layers 62 and 66 of the heater 60 may be the same as or different from the insulating layers 42 and 46 of the reference electrode 40.

The heater electrode 64 serves to generate heat and heat the external sensing electrode 22 to a temperature at which ionic conductivity is achieved. Various materials exhibiting an exothermic property due to electric resistance being supplied with power may be used as a material of the heater electrode 64, and preferably platinum, alumina, lead, a mixture of platinum and lead, and/or a mixture of platinum and alumina may be used as the material of the heater electrode 64.

The tunnel sheet 68 serves to insulate the tunnel electrode 70 from the stacked gas sensor 100 except for the tunnel electrode 70. Various insulating materials may be used as a material of the tunnel sheet 68, and preferably alumina may be used as the material of the tunnel sheet 68.

The tunnel electrode 70 serves to connect the gas sensor 100 to an external terminal which supplies power to the gas sensor 100. Various materials having conductivity may be used as a material of the tunnel electrode 70, and preferably platinum, alumina, and/or a mixture of platinum and alumina may be used as the material of the tunnel electrode 70.

In a gas sensor including the porous protective layer according to the present invention, at least one surface of the gas sensor 100, preferably one surface including an external sensing electrode, may be covered by the above-described porous protective layer according to the present invention. Specifically, the porous protective layer 200 may cover all of upper, lower, left, and right slopes of the gas sensor 100 as illustrated in FIG. 17, and the porous protective layer 200' may be implemented to cover only an upper portion of one surface of the gas sensor 100' including the external sensing electrode 22' as illustrated in FIG. 19. A portion which covers outer surfaces of the gas sensor other than one surface of the gas sensor including the external sensing electrode may be differently selected according to application.

According to one exemplary embodiment of the present invention, a thickness of the porous protective layer 200, which is formed on at least one surface of the gas sensor 100, may range from 20 to 200 µm, and may preferably range from 50 to 100 µm.

Detailed Description of the Invention

The present invention will be described in more detail with reference to the following embodiments, but the following embodiments are not limited to the scope of the present invention and should be interpreted to help understanding of the present invention.

EXAMPLE 1

A degree of deformation of a zirconia powder manufactured by performing a ball milling process on a zirconia powder having a particle diameter of 30 µm for 30 minutes is 1.8. A paste containing 70 g of a zirconia powder having a hexagonal cross section as illustrated in FIG. 10, 12 g of polyvinyl butyral as a binder component, 25 g of butyl alcohol as a solvent, and 30 g of graphite having a diameter of 5 µm as a pore former was applied to four surfaces of a stacked oxygen gas sensor including a platinum external sensing electrode having the structure shown in FIG. 18 so that an average thickness thereof after sintering became 70 µm, the pore former broke-down by a temperature being increased to 800° C. and an oxidation process being performed at the temperature of 800° C. for 1 hour, the temperature was increased to 1,450° C. again and maintained for 3 hours, and a gas sensor including a porous protective layer as illustrated in the following Table 1 was then prepared.

EXAMPLES 2 to 9

Gas sensors including porous protective layers as illustrated in the following Tables 1 and 2 were prepared by performing preparation in the same manner as in Example 1 and then changing a degree of deformation of the ceramic powder as illustrated in the following Table 1.

EXAMPLES 10 to 12

Gas sensors including porous protective layers as illustrated in the following Table 3 were prepared by performing preparation in the same manner as in Example 1, and were prepared by dipping a gas sensor on which the porous protective layer prepared in Example 1 is formed into a mixed solution of zirconia having a particle diameter of 0.8 µm, butyl alcohol, and polyvinylidene fluoride (concentrations were changed to 20 parts by weight of polyvinylidene fluoride and 50 parts by weight, 100 parts by weight, and 150 parts by weight of the zirconia powder, respectively, parts by weight based on 100 parts by weight of butyl alcohol), pressurizing the mixed solution at 4 atm for 20 minutes, and performing thermal processing at a temperature of 1,300° C. for 3 hours.

COMPARATIVE EXAMPLES 1 and 2

Gas sensors including porous protective layers as illustrated in the following Table 2 were prepared by performing preparation in the same manner as in Example 1 and were prepared by changing a degree of deformation of a ceramic powder as illustrated in the following Table 1.

COMPARATIVE EXAMPLE 3

A gas sensor including a porous protective layer as illustrated in the following Table 2 was prepared by performing preparation in the same manner as in Example 1 and was prepared without a binder component.

EXPERIMENTAL EXAMPLE 1

The following physical properties of the gas sensors including the porous protective layers prepared in Examples 1 to 12 and Comparative Examples 1 to 3 were measured and are shown in the following Table 1 to 3.

1. Measurement of Diameter and Porosity of Pore

After scanning electron microscope (SEM) photographs with respect to four portions having a thickness of 20%, a thickness of 40%, a thickness of 60%, and a thickness of 80% based on a surface abutting the gas sensor were captured by cutting the prepared porous protective layers in a direction perpendicular to one surface of the gas sensor, an average diameter and porosity of pores included in an area of 100 μm×100 μm were measured.

Also, after SEM photographs with respect to a first surface abutting one surface of the gas sensor and a second surface opposite to the first surface were captured, an average diameter of pores included in the area of 100 μm×100 μm was measured, and a ratio of pores included in a range of having an average diameter of ±2 μm of the second surface to diameters of the pores at the second surface was calculated.

2. Presence or Absence of Cracks in Gas Sensor

10 μl water drops were dropped 20 times onto the porous protective layer in a state in which the gas sensor was heated to have a temperature of 800° C. After the dropping, the porous protective layer was separated, and the presence or absence of cracks in the gas sensor was observed by an optical microscope using a red check (a method of applying a red penetrant to a surface). A case in which cracks did not occur is denoted as 0 and cases are denoted as 1 to 5 according to severity of crack occurrence.

3. Evaluation of Output of Gas Sensor

An output of each of the gas sensors were measured in a state in which the gas sensor was heated to have a temperature of 700° C., and a change rate of the output of the gas sensor was calculated by the following Equation 1. Since a gas diffusion resistance of the porous protective layer was reduced and a gas was smoothly supplied to the gas sensor as the change rate of the output of the gas sensor approached zero, a reduction of the output of the gas sensor was suppressed. A stacked oxygen gas sensor not including a porous protective layer was used as a base gas sensor.

$$\text{change rate of outputs of gas sensor} = \frac{\text{outputs of gas sensor} - \text{outputs of base gas sensor}}{\text{outputs of base gas sensor}} \times 100 \quad \text{[Equation 1]}$$

4. Evaluation of Strength of Porous Protective Layer

After a blue tape (Duct tape 3015 produced by 3M Company) was attached to an upper portion of the porous protective layer for strength measurement of the porous protective layer, whether the porous protective layer was observed on the blue tape when the blue tape was detached was evaluated. A case in which the porous protective layer was not observed at all is denoted as 0, and cases are denoted as 1 to 5 according to the extent of the observed porous protective layer.

5. Evaluation of Whether Gas Sensor Surface was Damaged

After the porous protective layer was separated from the gas sensor, whether the gas sensor was damaged due to the porous protective layer was evaluated by observing the surface of the gas sensor through an optical microscope. As a result of observation, a case in which the surface of the gas sensor was not damaged by pressing, scratching, or the like is denoted as 0, and cases are denoted as 1 to 5 according to the severity of damage.

TABLE 1

|  |  |  | Example 1 | Example 2 | Example 3 | Example 4 | Example 5 | Example 6 |
|---|---|---|---|---|---|---|---|---|
| Composition | Ceramic Powder | First Ceramic Powder (Degree of Deformation/wt %) | 1.7/100 | 2.4/100 | 4.0/100 | 4.5/100 | 5.5/100 | 1.7/30 |
|  |  | Second Ceramic Powder (Degree of Deformation/wt %) | — | — | — | — | — | 3.6/70 |
| Porous Protective Layer | | Porosity (%) | 42 | 49 | 62 | 63 | 75 | 56 |
| | | Pore Average Diameter (μm) | 11.6 | 14.1 | 21.5 | 23.8 | 29.1 | 16.2 |
| | | Second Surface Pore Diameter Uniformity (%) | 73 | 71 | 72 | 69 | 62 | 83 |
| Gas Sensor | | Presence or Absence of Cracks | 2 | 2 | 2 | 2 | 4 | 1 |
| | | Evaluation of Output of Gas Sensor | −1.8 | −1.7 | −1.4 | −1.5 | −1.6 | −1.4 |
| | | Evaluation of Strength | 1 | 1 | 1 | 1 | 3 | 0 |

TABLE 1-continued

|  | Example 1 | Example 2 | Example 3 | Example 4 | Example 5 | Example 6 |
|---|---|---|---|---|---|---|
| Whether Gas Sensor Surface was Damaged | 0 | 0 | 1 | 2 | 3 | 1 |

TABLE 2

| | | | Example 7 | Example 8 | Example 9 | Comparative Example 1 | Comparative Example 2 | Comparative Example 3 |
|---|---|---|---|---|---|---|---|---|
| Composition | Ceramic Powder | First Ceramic Powder (Degree of Deformation/wt %) | 1.7/40 | 1.7/80 | 1.7/45 | 1.0/100 | 1.3/100 | 1.7/100 |
| | | Second Ceramic Powder (Degree of Deformation/wt %) | 3.6/60 | 3.6/20 | 1.2/55 | — | — | — |
| Porous Protective Layer | | Porosity (%) | 49 | 45 | 27 | 18 | 24 | 8 |
| | | Pore Average Diameter (μm) | 16.7 | 13.3 | 8.8 | 2.7 | 3.9 | 1.2 |
| | | Second Surface Pore Diameter Uniformity (%) | 75 | 73 | 69 | 87 | 81 | 87 |
| Gas Sensor | | Presence or Absence of Cracks | 2 | 2 | 4 | 5 | 5 | 5 |
| | | Evaluation of Output of Gas Sensor | −1.8 | −1.7 | −4.3 | −8.8 | −6.9 | −17.8 |
| | | Evaluation of Strength | 1 | 1 | 3 | 5 | 4 | 4 |
| | | Whether Gas Sensor Surface was Damaged | 1 | 0 | 0 | 0 | 0 | 0 |

TABLE 3

| | | | Example 10 | Example 11 | Example 12 |
|---|---|---|---|---|---|
| Composition | Ceramic Powder | First Ceramic Powder (Degree of Deformation/wt %) | 1.7/100 | 1.7/100 | 1.7/100 |
| | | Second Ceramic Powder (Degree of Deformation/wt %) | — | — | — |
| Porous Protective Layer | | Porosity (%) | 40 | 38 | 38 |
| | | Pore Average Diameter (μm) | 8.7 | 6.3 | 4.9 |
| | | First Surface Pore Average Diameter (μm) | 11.8 | 11.5 | 10.6 |
| | | Second Surface Pore Average Diameter (μm) | 7.1 | 3.7 | 1.6 |
| | | Second Surface Pore Average Diameter:First Surface Pore Average Diameter | 1:1.6 | 1:3.1 | 1:6.6 |
| | | Second Surface Pore Diameter Uniformity (%) | 72 | 71 | 87 |
| Gas Sensor | | Presence or Absence of Cracks | 1 | 0 | 0 |
| | | Evaluation of Output of Gas Sensor | −1.5 | −1.2 | −3.2 |
| | | Evaluation of Strength | 1 | 0 | 0 |
| | | Whether Gas Sensor Surface is Damaged | 0 | 0 | 0 |

Specifically, as can be seen from Tables 1 and 2, it may be confirmed that less cracks of the gas sensor were generated in Examples 1 to 9 including a ceramic powder having a degree of deformation of 1.5 or more than were generated in Comparative Examples 1 and 2, an output of the gas sensors was very excellent, and the strength of the porous protective layers was extremely good.

Also, it may be confirmed that the gas sensor in Comparative Example 3 including the porous protective layer prepared without the pore former was not significantly improved in terms of cracking, performance, and strength of the sensor.

Also, through Examples 1 to 5, it may be confirmed that the performance of the gas sensors in Examples 1 to 3 was improved as the degree of deformation of the ceramic powder was increased. However, it may be confirmed that, in Example 4 using the ceramic powder having a degree of deformation of 4.2 and Example 5 using the ceramic powder having a degree of deformation of 5.5, an electrode on the surface of each of the gas sensor was damaged by the high degree of deformation and thus the performance of the gas sensor was slightly reduced.

Also, in Examples 6 to 8 using the ceramic powders having different degrees of deformation, it may be confirmed that the performance of the gas sensor in Example 6, in which a first ceramic powder and a second ceramic powder were included at a weight ratio range according to the present invention, was better than the performance of the gas sensors in Examples 7 and 8, and the occurrence of cracks in the gas sensor was reduced.

Also, in the gas sensor in Example 9, in which 40 wt % of the ceramic powder having a degree of deformation of 1.5 or more was included, it may be confirmed that the occurrence of cracks was significantly increased, the output of the gas sensor was also significantly increased, and the strength of the porous protective layer was reduced.

Also, as can be seen from Table 3, in Examples 10 to 12, which are the gas sensors in which a pore diameter of a first surface of the porous protective layer and a pore diameter of the second surface was adjusted, in the gas sensor in Example 11 it may be confirmed that cracks did not occur due to a diameter gradient in which the diameter of the pore was increased as they approached the first surface, the output of the gas sensor was very good, the second surface abutting the atmosphere was dense and the strength thereof was improved, and there was no damage on the surface of the gas sensor. On the other hand, in the gas sensor in Example 10, it may be confirmed that the diameter of the pore was reduced toward the first surface of the gas sensor and cracks occurred. In the gas sensor in Example 12, it may be confirmed that the output of the gas sensor was significantly reduced.

EXAMPLE 13

(1) A composition including 35 g of yttrium-stabilized zirconia powder, 6 g of polyvinyl butyral as a binder component, 35 g of butyl alcohol as a solvent, 5 g of TEOS, and 120 g of polystyrene-B-polyethylene oxide as an amphiphilic copolymer expressed by the following Chemical Formula 1 was dipped onto a sensing electrode of a stacked oxygen gas sensor including a platinum sensing electrode having the structure shown in FIG. 17 for 3 minutes, and a temperature of 28° C. was maintained for 250 minutes for coating.

A total molecular weight of the amphiphilic block copolymer was 29,000, a molecular weight of polyethylene oxide (PEO) was 5,000 (17.2%), a polydispersity index (PDI) was 1.09, and a monomer mole fraction of polystyrene and polyethylene oxide was 0.64:0.36.

[Chemical Formula 1]

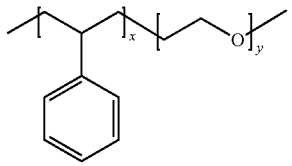

(2) Gas sensors including porous protective layers as illustrated in Table 4 were prepared by sintering the coated composition at a temperature of 1,100° C. so that an average thickness after sintering became 70 μm.

EXAMPLES 14 to 17

Gas sensors including porous protective layers as illustrated in Table 4 were prepared by performing preparation in the same manner as in Example 13 and were prepared by changing the content of PS-b-PEO included in the composition as illustrated in the following Table 4.

EXAMPLES 18 to 21

Gas sensors including porous protective layers as illustrated in the following Table 5 were prepared by dipping the gas sensors including porous protective layers prepared by performing preparation in the same manner as in Example 14 into a mixed solution of zirconia having a particle diameter of 0.8 μm, butyl alcohol, and polyvinylidene fluoride (concentrations were changed with 20 parts by weight of polyvinylidene fluoride and 50 parts by weight, 100 parts by weight, and 150 parts by weight of zirconia powder, respectively, parts by weight based on 100 parts by weight of butyl alcohol), pressurizing the mixed solution at 4 atm for 20 minutes, and performing thermal processing at a temperature of 1,300° C. for 3 hours.

COMPARATIVE EXAMPLES 4 to 7

Gas sensors including porous protective layers as illustrated in the following Table 6 were prepared by performing preparation in the same manner as in Example 14 and were prepared by changing an amphiphilic block copolymer in the composition as illustrated in the following Table 6.

EXPERIMENTAL EXAMPLE 2

The following physical properties of the gas sensors including the porous protective layers prepared through Examples 13 to 21 and Comparative Examples 4 to 7 were measured and are shown in the following Tables 4 to 6.

1. Measurement of Diameter of Pores, Average Porosity Per Unit Volume, and Whether Continuous Pores were Formed After SEM photographs with respect to four portions having a thickness of 20%, a thickness of 40%, a thickness of 60%, and a thickness of 80% based on a surface abutting the gas sensor were captured by cutting the prepared porous protective layer in a direction perpendicular to one surface of the gas sensor, an average diameter of pores, an average porosity per unit volume, and whether continuous pores included in an area of 100 μm×100 μm were formed were measured.

Meanwhile, a continuous pore formation rate was measured based on an amount of pores included in the porous protective layer.

2. Presence or Absence of Cracks in Gas Sensor

10 μl water drops were dropped 20 times onto the porous protective layer in a state in which the gas sensor was heated to have a temperature of 800° C. After the dropping, the porous protective layer was separated, and the presence or absence of cracks in the gas sensor was observed through an optical microscope by a red check (a method of applying a red impregnation liquid to a surface). A case in which cracks did not occur is denoted as 0 and cases are denoted as 1 to 5 according to severity of crack occurrence.

3. Evaluation of Output of Gas Sensor

Output of the gas sensor was measured in a state in which the gas sensor was heated to have a temperature of 700° C., and a change rate of the output of the gas sensor was calculated by Equation 1 in Experimental Example 1. Since a gas diffusion resistance of the porous protective layer was reduced and a gas was smoothly supplied to the gas sensor as the change rate of the output of the gas sensor approached zero, a reduction of the output of the gas sensor was suppressed. A stacked oxygen gas sensor not including the porous protective layer was used as a base gas sensor.

TABLE 4

|  |  | Example 13 | Example 14 | Example 15 | Example 16 | Example 17 |
|---|---|---|---|---|---|---|
| Composition | Zirconia Powder (g) | 35 | 35 | 35 | 35 | 35 |
|  | Polyvinylidene Fluoride (g) | 6 | 6 | 6 | 6 | 6 |
|  | Butyl Alcohol (g) | 35 | 35 | 35 | 35 | 35 |
|  | Tetraethylorthosilicate (TEOS) (g) | 5 | 5 | 5 | 5 | 5 |
|  | Polystyrene-B-Polyethylene Oxide (PS-b-PEO) (g) | 120 | 160 | 200 | 280 | 80 |
|  | Alumina Powder + TEOS:PS-b-PEO Weight Ratio | 1:3 | 1:4 | 1:5 | 1:7 | 1:2 |
| Porous Protective Layer | Pore Average Diameter | 24.9 μm | 25.1 μm | 26.3 μm | 23.9 μm | 24.5 μm |
|  | Continuous Pore Formation Rate | 85% | 91% | 87% | 23% | 21% |
|  | Average Porosity per Unit Volume | 38% | 42% | 43% | 47% | 41% |
| Gas Sensor | Presence or Absence of Cracks | 2 | 2 | 2 | 2 | 2 |
|  | Evaluation of Output of Gas Sensor | −2.4 | −2.2 | −2.3 | −25.9 | −23.1 |

TABLE 5

|  |  | Example 18 | Example 19 | Example 20 | Example 21 |
|---|---|---|---|---|---|
| Composition | Zirconia Powder (g) | 35 | 35 | 35 | 35 |
|  | Polyvinylidene Fluoride (g) | 6 | 6 | 6 | 6 |
|  | Butyl Alcohol (g) | 35 | 35 | 35 | 35 |
|  | TEOS (g) | 5 | 5 | 5 | 5 |
|  | PS-b-PEO (g) | 160 | 160 | 160 | 160 |
|  | Alumina Powder + TEOS:PS-b-PEO Weight Ratio | 1:4 | 1:4 | 1:4 | 1:4 |
| Porous Protective Layer | First Surface Pore Average Diameter | 25.1 μm | 25.2 μm | 25.0 μm | 25.1 μm |
|  | Second Surface Pore Average Diameter | 13.2 μm | 9.0 μm | 6.1 μm | 3.2 μm |
|  | Second Surface Pore Average Diameter:First Surface Pore Average Diameter | 1:1.9 | 1:2.8 | 1:4.1 | 1:7.8 |
|  | Continuous Pore Formation Rate | 90% | 89% | 91% | 88% |
|  | Average Porosity per Unit Volume | 42% | 40% | 39% | 39% |
| Gas Sensor | Presence or Absence of Cracks | 1 | 1 | 1 | 0 |
|  | Evaluation of Output of Gas Sensor | −1.9 | −1.7 | −1.9 | −10.9 |

TABLE 6

|  |  | Comparative Example 4 | Comparative Example 5 | Comparative Example 6 | Comparative Example 7 |
|---|---|---|---|---|---|
| Composition | Zirconia Powder (g) | 35 | 35 | 35 | 35 |
|  | Polyvinylidene Fluoride (g) | 6 | 6 | 6 | 6 |
|  | Butyl Alcohol (g) | 35 | 35 | 35 | 35 |
|  | TEOS (g) | 5 | 5 | 5 | 5 |
|  | Graphite powder (g) | — | 160 | — | — |

TABLE 6-continued

|  |  | Comparative Example 4 | Comparative Example 5 | Comparative Example 6 | Comparative Example 7 |
|---|---|---|---|---|---|
|  | Polystyrene (g) | — | — | 160 | — |
|  | Polyethylene Oxide (g) | — | — | — | 160 |
| Porous Protective Layer | Pore Average Diameter | 5.3 μm | 3.0 μm | 2.8 μm | 2.8 μm |
|  | Continuous Pore Formation Rate | 6% | 11% | 6% | 6% |
|  | Average Porosity per Unit Volume | 7% | 14% | 9% | 8% |
| Gas Sensor | Presence or Absence of Cracks | 1 | 1 | 1 | 1 |
|  | Evaluation of Output of Gas Sensor | −35.8 | −30.9 | −36.8 | −36.8 |

Specifically, as can be seen from Tables 4 to 6, in a comparison of Examples 13 to 15 and Examples 16 to 17, 80% or more continuous pores were formed in Examples 13 to 15, in which a ratio of a gross weight of alumina powder and TEOS to a weight of poly(styrene)-b-poly(acrylamide) ranged from 1:3 to 1:5. However, 30% or less continuous pores were formed in Examples 16 and 17, in which a weight ratio was out of the above weight ratio. Also, it may be confirmed that the outputs of the gas sensors in Examples 13 to 15 were better than those in Examples 16 and 17.

Also, in a comparison of Examples 18 to 20 and Example 21, it may be confirmed that outputs of the gas sensors in Examples 18 to 20, in which a ratio of the diameter of the second surface of the porous protective layer to the diameter of the first surface ranged from 1:1.9 to 1:4.1 were better than those in Example 21, in which a ratio of the diameter of the second surface of the porous protective layer to the diameter of the first surface was 1:7.8. In other words, it may be confirmed that no cracks occurred in Example 21 and the output of the gas sensor was worse than those in Examples 18 to 20.

Also, in a comparison of Examples 18 to 20 and Examples 13 to 15, it may be confirmed that the outputs of the gas sensors in Examples 18 to 20 were better than those in Examples 13 to 15 and less cracks occurred in Examples 18 to 20 than in Examples 13 to 15.

Finally, in a comparison of Examples 13 to 15 and Comparative Examples 4 to 7, unlike Examples 13 to 15, the continuous pore formation rate in Comparative Example 4, in which poly(styrene)-b-poly(acrylamide) was not included, the continuous pore formation rate in Comparative Example 5, in which zirconia rather than poly(styrene)-b-poly(acrylamide) was included, the continuous pore formation rate in Comparative Example 6, in which polystyrene rather than poly(styrene)-b-poly(acrylamide) was included, and the continuous pore formation rate in Comparative Example 7, in which polyethylene oxide rather than poly(styrene)-b-poly(acrylamide) was included, were significantly reduced as compared to the continuous pore formation rates in Examples 13 to 15. Also, it may be confirmed that the outputs of the gas sensors in Examples 13 to 15 were better than those in Comparative Examples 4 to 7 and less cracks occurred in Examples 13 to 15 than in Comparative Examples 4 to 7.

EXAMPLE 22

(1) A composition including 70 g of yttrium-stabilized zirconia powder, 12 g of polyvinyl butyral as a binder component, 25 g of butyl alcohol as a solvent, and 30 g of PET fibers (having a fineness of 0.5 denier at one end, a fineness of 3 denier at the other end, a meting point of 90° C., and a fiber length of 100 μm), which is a low melting point fiber, was applied to a sensing electrode of a stacked oxygen gas sensor including a platinum sensing electrode having the structure shown in FIG. 17, and the low melting point staple fiber was broken-down by heating at a temperature of 300° C.

The low melting point staple fiber of the composition was designed so that one end thereof was located on a first surface facing the sensing electrode and the other end thereof was located on a second surface opposite to the first surface.

(2) Gas sensors including porous protective layers as illustrated in Table 7 were prepared by sintering a composition in which low melting point staple fibers broke-down at a temperature of 1,450° C. so that an average thickness after sintering became 70 μm.

EXAMPLES 23 to 31

Gas sensors including porous protective layers as illustrated in Tables 7 and 8 were prepared by performing preparation in the same manner as in Example 22 and were prepared by changing the type of PET fiber as illustrated in Tables 7 and 8.

COMPARATIVE EXAMPLES 8 and 9

Gas sensors including porous protective layers as illustrated in Table 9 were prepared by performing preparation in the same manner as in Example 22 and were prepared by changing the type of PET fiber as illustrated in Table 9.

COMPARATIVE EXAMPLES 10 and 11

Gas sensors including porous protective layers as illustrated in Table 9 were prepared by performing preparation in the same manner as in Example 22 and were prepared by changing the type of PET fiber as illustrated in Table 9 and designing the low melting point staple fiber of the composition to be located in a direction parallel to the sensing electrode.

EXPERIMENTAL EXAMPLE 3

The following physical properties of the gas sensors including the porous protective layers prepared through Examples 22 to 31 and Comparative Examples 8 to 11 were measured and are shown in the following Tables 7 to 9.

1. Measurement of Diameter of Pores, Whether Carbide of Pore was Formed, and an Average Porosity Per Unit Volume After SEM pictures with respect to four portions having a thickness of 20%, a thickness of 40%, a thickness of 60%, and a thickness of 80% based on a surface abutting the gas sensor were captured by cutting the prepared porous protective layer in a direction perpendicular to one surface of the gas sensor, an average diameter of pores included in an area of 100 μm×100 μm, whether carbide of the pore was formed, and an average porosity per unit volume were measured.

2. Presence or Absence of Cracks in Gas Sensor

10 μl water drops were dropped 20 times onto the porous protective layer in a state in which the gas sensor was heated to have a temperature of 800° C. After the dropping, the porous protective layer was separated, and the presence or absence of cracks in the gas sensor was observed through an optical microscope by a red check (a method of applying red impregnation liquid to a surface). A case in which cracks did not occur is denoted as 0 and cases are denoted as 1 to 5 according to severity of crack occurrence.

3. Evaluation of Output of Gas Sensor

An output of the gas sensor was measured in a state in which the gas sensor was heated to have a temperature of 700° C., and a change rate of the output of the gas sensor was calculated by Equation 1 in Experimental Example 1. Since a gas diffusion resistance of the porous protective layer was reduced and a gas was smoothly supplied to the gas sensor as the change rate of the outputs of the gas sensor approached zero, a reduction of the outputs of the gas sensor was suppressed. A stacked oxygen gas sensor not including the porous protective layer was used as a base gas sensor.

TABLE 7

|  |  | Example 22 | Example 23 | Example 24 | Example 25 | Example 26 |
|---|---|---|---|---|---|---|
| PET Fiber | Fineness of One End | 0.5D | 0.5D | 0.5D | 0.5D | 1D |
|  | Fineness of Other End | 3D | 2.5D | 2D | 1.5D | 3D |
|  | Meting Point | 90° C. | 90° C. | 90° C. | 90° C. | 90° C. |
| Porous Protective Layer | First Surface Pore Average Diameter | 5.8 μm | 5.8 μm | 5.8 μm | 5.8 μm | 11.1 μm |
|  | Second Surface Pore Average Diameter | 34.22 μm | 27.84 μm | 22.62 μm | 17.98 μm | 32.19 μm |
|  | Second Surface Pore Average Diameter:First Surface Pore Average Diameter | 1:5.9 | 1:4.8 | 1:3.9 | 1:3.1 | 1:2.9 |
|  | Average Porosity per Unit Volume | 41% | 39% | 37% | 35% | 43% |
|  | Whether Carbide of Pore was Formed | X | X | X | X | X |
| Gas Sensor | Presence or Absence of Cracks | 1 | 1 | 1 | 1 | 2 |
|  | Evaluation of Output of Gas Sensor | −3.1 | −2.9 | −2.3 | −1.9 | −2.1 |

TABLE 8

|  |  | Example 27 | Example 28 | Example 29 | Example 30 | Example 31 |
|---|---|---|---|---|---|---|
| PET Fiber | Fineness of One End | 1D | 1.5D | 0.5D | 1.5D | 3D |
|  | Fineness of Other End | 2D | 3D | 4D | 1.5D | 3D |
|  | Meting Point | 90° C. | 90° C. | 90° C. | 90° C. | 90° C. |
| Porous Protective Layer | First Surface Pore Average Diameter | 11.1 μm | 17.2 μm | 5.8 μm | 17.98 μm | 32.19 μm |
|  | Second Surface Pore Average Diameter | 22.61 μm | 30.96 μm | 44.66 μm | 17.98 μm | 32.19 μm |
|  | Second Surface Pore Average Diameter:First Surface Pore Average Diameter | 1:1.9 | 1:1.8 | 1:7.7 | 1:1 | 1:1 |
|  | Average Porosity per Unit Volume | 40% | 45% | 45% | 41% | 54% |
|  | Whether Carbide of Pore was Formed | X | X | X | X | X |
| Gas Sensor | Presence or Absence of Cracks | 2 | 2 | 2 | 3 | 4 |
|  | Evaluation of Output of Gas Sensor | −1.6 | −1.5 | −10.3 | −7.3 | −8.3 |

TABLE 9

|  |  | Comparative Example 8 | Comparative Example 9 | Comparative Example 10 | Comparative Example 11 |
|---|---|---|---|---|---|
| PET Fiber | Fineness of One End | 0.5D | 1D | 0.5D | 1D |
|  | Fineness of Other End | 1.5D | 2D | 1.5D | 2D |

TABLE 9-continued

|  |  | Comparative Example 8 | Comparative Example 9 | Comparative Example 10 | Comparative Example 11 |
|---|---|---|---|---|---|
| Porous Protective Layer | Meting Point | 250° C. | 250° C. | 90° C. | 90° C. |
|  | First Surface Pore Average Diameter | 5.2 μm | 10.7 μm | Pores were formed in a direction parallel to a surface of a gas sensor. |  |
|  | Second Surface Pore Average Diameter | 15.6 μm | 19.38 μm |  |  |
|  | Second Surface Pore Average Diameter:First Surface Pore Average Diameter | 1:3 | 1:1.9 |  |  |
|  | Average Porosity per Unit Volume | 28% | 30% | 35% | 40% |
|  | Whether Carbide of Pore was Formed | 0 | 0 | X | X |
| Gas Sensor | Presence or Absence of Cracks | 3 | 3 | 3 | 4 |
|  | Evaluation of Output of Gas Sensor | −12.3 | −12.2 | −15.8 | −14.5 |

Specifically, as can be seen from Tables 7 to 9, carbide of pores were not formed in Examples 22 to 31 using PET fiber having a melting point of 90° C., and carbide of pores were formed in Comparative Examples 8 and 9 using PET fiber having a melting point of 250° C.

Also, it may be confirmed that the outputs of the gas sensors in Examples 22 to 31 were better than those in Comparative Examples 8 and 9 and less cracks occurred in Examples 22 to 31 than in Comparative Examples 8 and 9.

Also, in a comparison of Examples 25 and 26 and Comparative Examples 10 and 11, the outputs of the gas sensors in Examples 25 and 26, in which pores were formed in a direction perpendicular to the abutting surface of the gas sensors, were better than those in Comparative Examples 10 and 11, in which the pores were formed in a direction parallel to the abutting surface of the gas sensors, and less cracks occurred in Examples 25 and 26 than in Comparative Examples 10 and 11.

Also, in a comparison of Examples 22 to 28 and Example 29, it may be confirmed that the outputs of the gas sensors in Examples 22 to 28, in which a ratio of the diameter of the second surface of the porous protective layer to the diameter of the first surface ranged from 1:1.8 to 1:5.9, were better than that in Example 29, in which a ratio of the diameter of the second surface of the porous protective layer to the diameter of the first surface was 1:7.7.

Also, it may be confirmed that the output of the gas sensor in Example 25, in which a diameter of the pore was increased from the second surface of the porous protective layer to the first surface, was better than that in Example 30, in which a size of the pore of the second surface of the porous protective layer was the same as that of the first surface, and less cracks occurred in Example 25 than in Example 30.

Also, it may be confirmed that the outputs of the gas sensor in Examples 26 to 28, in which a diameter of the pore was increased from the second surface of the porous protective layer to the first surface, were better than that in Example 31, in which a size of the pore of the second surface of the porous protective layer was the same as that of the first surface, and less cracks occurred in Examples 26 to 28 than in Example 31.

According to the present invention, a gas sensor can be protected from an external physical impact and external physical and chemical factors such as a liquid material and a poisonous material in a test gas, and an output of the gas sensor due to the external factors can be prevented from being reduced. Further, since a diffusion speed of a test gas is significantly increased by the pores being formed and the arrangement of the pores, a response speed to a target gas can be made to be very quick. Since influence of the external factors such as a poisonous material and the like on the gas sensor is prevented, sensitivity to the target gas may be very good and a concentration of the target gas can be accurately measured. Furthermore, since a porous protective layer for a gas sensor has extremely excellent mechanical properties, the pores do not collapse or cracks are not generated even in various types of impacts, performance of the gas sensor can be maintained, and durability can be significantly improved.

What is claimed is:

1. A method of manufacturing a porous protective layer for a gas sensor, the method comprising:
   (1) a step of introducing a composition for forming a porous protective layer including a pore former and a ceramic powder onto a sensing electrode for a gas sensor; and
   (2) a step of sintering the introduced composition for forming a porous protective layer;
   wherein the ceramic powder includes a first ceramic powder having a degree of deformation which ranges from 1.5 to 2.0 and a second ceramic powder having a degree of deformation which ranges from 3.0 to 4.2 expressed by the following Relational Formula 1, and $$\text{degree of deformation} = \frac{\text{diameter of circumscribed circle of cross section of ceramic powder (μm)}}{\text{diameter of inscribed circle of cross section of ceramic powder (μm)}} \quad [\text{Relational Formula 1}]$$

a weight ratio of the first ceramic powder to the second ceramic powder ranges from 1:1.6 to 1:3.0.

2. The method of claim 1, wherein, in step 1, the degree of deformation of the ceramic powder ranges from 1.8 to 4.2.

3. The method of claim 1, wherein a ceramic powder which satisfies a condition of the degree of deformation among ceramic powders in step (1) makes up 50 wt % or more of the entire ceramic powder.

4. A porous protective layer for a gas sensor comprising ceramic powders having a degree of deformation of 1.5 or more expressed by the following Relational Formula 1, wherein the porous protective layer is formed by welding at least one region of each particle of the ceramic powder to another particle of the ceramic powder;

$$\text{degree of deformation} = \frac{\text{diameter of circumscribed circle of cross section of ceramic powder (µm)}}{\text{diameter of inscribed circle of cross section of ceramic powder (µm)}}$$ [Relational Formula 1]

wherein the porous protective layer includes a first surface and a second surface opposite to the first surface, and has a diameter gradient having a pore diameter which increases from the second surface to the first surface and an average diameter of pores included in the second surface ranges from 5.5 to 8 µm, and pores having a pore diameter of ±2 µm of the average diameter make-up 80% or more of all of the pores included in the second surface.

5. A porous protective layer for a gas sensor, which protects a sensing electrode of a gas sensor, wherein the porous protective layer includes through pores passing through a first surface facing a sensing electrode and a second surface opposite to the first surface, and the through pores have a diameter which increases from the second surface of the porous protective layer to the first surface.

6. The porous protective layer for a gas sensor of claim 5, wherein, in the through pores, a ratio of the diameter of the second surface of the porous protective layer to a diameter of the first surface ranges from 1:1.8 to 1:6.

7. An electrode for a gas sensor comprising the porous protective layer for a gas sensor according to claim 4.

8. A gas sensor comprising the electrode for a gas sensor according to claim 7 as an external sensing electrode.

* * * * *